(12) United States Patent
Travan et al.

(10) Patent No.: US 11,953,481 B2
(45) Date of Patent: Apr. 9, 2024

(54) GAS SENSING DEVICE AND METHOD FOR DETERMINING A CALIBRATED MEASUREMENT VALUE FOR A CONCENTRATION OF A TARGET GAS

(71) Applicant: Infineon Technologies AG, Neubiberg (DE)

(72) Inventors: Caterina Travan, Munich (DE);
Cecilia Carbonelli, Munich (DE);
Ulrich Krumbein, Rosenheim (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 186 days.

(21) Appl. No.: 17/647,651

(22) Filed: Jan. 11, 2022

(65) Prior Publication Data

US 2022/0236244 A1 Jul. 28, 2022

(30) Foreign Application Priority Data

Jan. 22, 2021 (EP) .................................... 21153012

(51) Int. Cl.
| | |
|---|---|
| *G01N 33/00* | (2006.01) |
| *G01N 27/12* | (2006.01) |
| *G01N 27/02* | (2006.01) |
| *G01N 27/22* | (2006.01) |

(52) U.S. Cl.
CPC ......... *G01N 33/0006* (2013.01); *G01N 27/12* (2013.01); *G01N 33/0008* (2013.01); *G01N 33/0027* (2013.01); *G01N 33/0034* (2013.01); *G01N 27/028* (2013.01); *G01N 2027/222* (2013.01)

(58) Field of Classification Search
CPC .. G01N 21/3504; G01N 21/314; G01N 21/61;
G01N 21/93; G01N 33/0006; G01N 35/00693; G01N 2021/933; G01N 2035/00702; G01N 2223/638
See application file for complete search history.

(56) References Cited

U.S. PATENT DOCUMENTS

| | | | | |
|---|---|---|---|---|
| 2004/0244151 A1* | 12/2004 | Sakata | ............. | G01N 33/48771 23/306 |
| 2006/0155486 A1* | 7/2006 | Walsh | ................ | G01N 33/0034 702/32 |
| 2014/0238100 A1 | 8/2014 | Londergan et al. | | |
| 2015/0360171 A1* | 12/2015 | Mizuno | ................ | G01N 33/004 73/31.07 |

FOREIGN PATENT DOCUMENTS

| | | |
|---|---|---|
| CN | 106405007 B | 10/2018 |
| WO | 2020107445 A1 | 6/2020 |

* cited by examiner

*Primary Examiner* — Benjamin R Schmitt
(74) *Attorney, Agent, or Firm* — Slater Matsil, LLP

(57) ABSTRACT

A method for determining a calibrated measurement value for a concentration of the target gas comprises obtaining a measurement signal based on the concentration of the target gas. The method further comprises determining the calibrated measurement value based on the measurement signal and based on a calibration model. The calibration model is based on calibration data of a plurality of test sensor units having the same type as the sensor unit.

20 Claims, 14 Drawing Sheets

GAS SENSING DEVICE AND METHOD FOR DETERMINING A CALIBRATED MEASUREMENT VALUE FOR A CONCENTRATION OF A TARGET GAS This application claims the benefit of European Patent Application No. 21153012, filed on Jan. 22, 2021, which application is hereby incorporated herein by reference.

TECHNICAL FIELD

Examples of the present disclosure relate to a gas sensing device, in particular a chemoresistor gas sensing device, for sensing a target gas. Further examples relate to a method for determining a calibrated measurement value for a concentration of a target gas. Some examples relate to a method for calibrating a gas sensing device.

BACKGROUND

Chemoresistive gas sensors, like metal-oxide- (MOX), polymer- or graphene-based gas sensors, often exhibit variations of their properties from device to device since the deposition of the sensing layer is usually difficult to control, therefore leading, for instance, to different sensing area. Due to these variations those sensors are usually calibrated one by one, exposing them to certain concentrations of the target gases and storing the calibration data into the sensor itself (e.g. in ASIC or μC registers). This calibration data will be used by the software to estimate the concentration of the target gases, e.g. with polynomial fitting or adjusting a model of the sensor.

SUMMARY

In view of the state of the art, a concept for a gas sensing device would be desirable, which provides an improved trade-off between a time- and cost-efficient calibration of the gas sensing device and a high accuracy of the gas sensing device in determining a concentration of the target gas.

Examples of the present disclosure provide a gas sensing device for sensing a target gas. The gas sensing device comprises a sensing unit for sensing the target gas. The sensing unit is configured for providing a measurement signal based on a concentration of the target gas in an environment of the gas sensing device. The gas sensing device further comprises a signal calibration unit which is configured for determining a calibrated measurement value based on the measurement signal and further based on a calibration model. The calibration model is based on calibration data of a plurality of test sensor units having the same type as the sensor unit.

Further examples of the present disclosure provide a method for determining a calibrated measurement value for a concentration of the target gas. The method comprises a step of obtaining a measurement signal based on the concentration of the target gas. The method further comprises a step of determining the calibrated measurement value based on the measurement signal and based on a calibration model. The calibration model is based on calibration data of a plurality of test sensor units having the same type as the sensor unit.

BRIEF DESCRIPTION OF THE DRAWINGS

Embodiments of the present disclosure are described in more detail below with respect to the figures, among which.

DETAILED DESCRIPTION OF ILLUSTRATIVE EMBODIMENTS

In the following, embodiments are discussed in detail, however, it should be appreciated that the embodiments provide many applicable concepts that can be embodied in a wide variety of sensing devices and calibration thereof. The specific embodiments discussed are merely illustrative of specific ways to implement and use the present concept, and do not limit the scope of the embodiments. In the following description, a plurality of details is set forth to provide a more thorough explanation of embodiments of the disclosure. However, it will be apparent to one skilled in the art that other embodiments may be practiced without these specific details. In other instances, well-known structures and devices are shown in form of a block diagram rather than in detail in order to avoid obscuring examples described herein. In addition, features of the different embodiments described herein may be combined with each other, unless specifically noted otherwise.

In the following description of embodiments, the same or similar elements or elements that have the same functionality are provided with the same reference sign or are identified with the same name, and a repeated description of elements provided with the same reference number or being identified with the same name is typically omitted. Hence, descriptions provided for elements having the same or similar reference numbers or being identified with the same names are mutually exchangeable or may be applied to one another in the different embodiments. Features shown in dashed lines are optional features.

Figure 1:
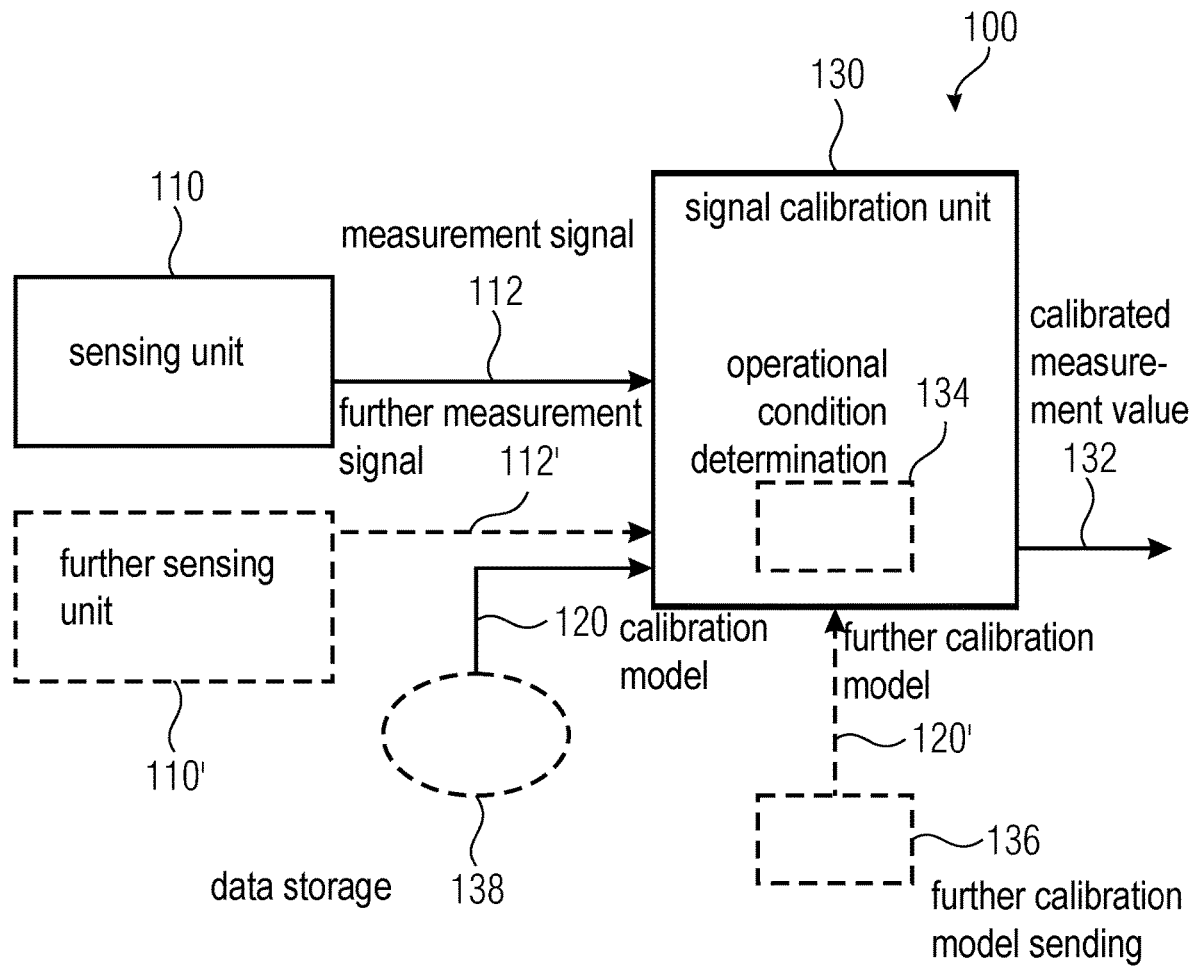
FIG. 1 illustrates an example of a gas sensing device.

FIG. 1 illustrates an example of a gas sensing device 100 for sensing a target gas. The gas sensing device 100 comprises a sensing unit 110 for sensing the target gas. The sensing unit 110 is configured for providing a measurement signal 112 based on a concentration of the target gas in an environment of the gas sensing device. The gas sensing device 100 further comprises a signal calibration unit 130. The signal calibration unit 130 is configured for determining a calibrated measurement value 132 based on the measurement signal 112 and based on a calibration model 120. The calibration model 120 is based on calibration data of a plurality of test sensor units having the same type as the sensor unit.

Examples of the present disclosure rely on the idea to determine the calibrated measurement value 132 for the concentration of the target gas by using the calibration model 120 which is based on calibration data of a plurality of test sensor units. As the plurality of test sensor units which have the same type as the sensor unit 110 may be representative of characteristics of the sensor unit 110 a calibration for the sensor unit 110 may at least partially be predicted from the calibration model 120. Therefore, an individual calibration of the sensor unit 110 may be avoided, or at least an extent to which the sensor unit 110 has to be calibrated individually may be reduced. Nevertheless, a high accuracy in the determination of the calibrated measurement value 112 may be achieved, as characteristics of the sensor unit 110 may be derived from the calibration model 120. In particular, as the calibration model 120 is based on a plurality of test sensing units, the calibration model 120 may be able to compensate for manufacturing variations between individual sensing units. Calibration of single devices is an expensive process usually done on package level which may drastically increases the price of the final product. Therefore, avoiding an individual calibration of the sensor unit 110 allows for a time- and cost-efficient manufacturing process of the gas sensing device 100. For example, the gas sensing device 100 is for monitoring outdoor and/or indoor air quality. Calibration costs for such gas sensors may represent a relevant part of the total cost. The disclosed concept reduces the calibration costs and therefore the overall costs of the gas sensing device.

Furthermore, during its lifetime, a gas sensing device, for example a chemoresistive sensor, is may be exposed to an event that temporarily or permanently modifies the original behavior of the gas sensing device. Therefore, determining the concentration of the target gas based on a device-individual calibration may reduce the accuracy for determining the concentration of the target gas after a change of the behavior of the gas sensing device. In the case of chemoresistive gas sensing devices, such an event may for example be an exposure to a high concentration of a gas which is adsorbed by the sensing unit, for example at a sensing layer of the sensing unit, and thus occupies at the adsorption sites. The adsorption may decrease the sensitivity of the sensor, or may degrade the sensing material due to poisoning or oxidation of the surface (for instance when the sensor is exposed to high concentration of $O_3$). Using the calibration model 120 has the advantage, that the determination of the calibrated measurement value 132 includes calibration data of sensing units which are different from the sensing unit 110, thus providing a broad knowledge base which may allow to cope with a change of the behavior of the sensing unit 110. Thus, the gas sensing device 100 may persistently determine the calibrated measurement value 132 with a high accuracy even without a recalibration after manufacturing.

As the calibration model 120 does not necessarily rely on calibration data of the sensing unit 110, it may further be updated without the need to subject the gas sensing device 100 to a recalibration procedure. For example, calibration data for updating the calibration model may be obtained from test sensing units or further sensing units.

In examples, the gas sensing device 100 is a chemoresistive gas sensing device. For example, the sensing unit 110 may comprise a chemoresistive sensing layer a surface region of which is exposed to the environment of the gas sensing device 100, and which may change its resistivity upon adsorption of gas molecules, in particular gas molecules of the target gas, at the surface reason of the sensing layer.

For example, the measurement signal 112 provided by the sensing unit 110 may be a digital or an analog signal. The measurement signal 112 may represent a resistivity of a sensing layer of the sensing unit 110 which depends on the concentration of the target gas in the environment of the sensing unit 110. The calibrated measurement signal 132 may represent the concentration of the target gas, and derive from the measurement signal 112 by using the calibration model 120.

For example, the calibration model 120 is stored on a data storage of the gas sensing device 100. The signal calibration unit 130 may be a signal processor of the gas sensing device 100 or may represent a process performed on a signal processor the gas sensing device 100.

In examples, the calibration model 120 is a statistical model which is trained by supervised learning techniques using the calibration data. Training the calibration model 120 using the calibration data of the plurality of test sensing units allows for an accurate determination of the calibrated measurement value 132 even if the calibration model 120 does not include calibration data of the sensing unit 110.

For example, the calibration model 120 is built using data obtained from a characterization of a statistically relevant amount of test sensing units.

The test sensing units may be selected so that the plurality of test sensing units is statistically representative of the sensing unit 110. For example, the test sensing units may be manufactured equivalently to the sensing unit 110.

In examples, the calibration data includes measurement signal values of the test sensor units. The measurement signal values of the test sensor units are acquired during a plurality of calibration measurement sequences. During the calibration measurement sequences, test sensor units of the plurality of test sensor units are exposed to a sequence of varying environmental conditions. The environmental conditions are characterized at least by one or more environmental parameters including a concentration of the target gas. For example, the environmental parameters may further include one or more of temperature, humidity, pressure, concentrations of one or more further gases, and further parameters. Generating the calibration data using a plurality of environmental parameters may increase a robustness of the calibration model. The calibration data may optionally include values for the environmental parameters during the sequence of varying environmental conditions. That is, the sequence of varying environmental parameters may follow a specific sequence of values of the environmental parameters. For example, the sequences of varying environmental parameters may follow sequences of varying concentrations of the target gas, while one or more further environmental parameters are kept constant during the sequence.

Including measurement signal values of the test sensing units obtained during the sequence of varying environmental conditions into the calibration model allows for an accurate determination of the calibrated measurement value 132 over a wide range of concentrations and of values of further environmental conditions. Comparing the behavior of the sensing unit 110 with the calibration model 120 which is based on measurement signal values of the test sensing units obtained during the sequence of varying concentrations may provide for a precise prediction of the calibrated measurement value 132.

In examples, the calibration data of the test sensor units includes respective baseline values of the test sensor units. For example, a baseline value may represent a value of the measurement signal, that is a measurement signal value, which is measured in a condition in which the sensing unit is exposed to an environment in which the concentration of the target gas is zero or substantially zero. The base line value may be measured particularly easy but may provide at least a hint on basic characteristics of the sensing unit. Thus, the baseline value may allow for a classification of the sensing unit. In combination with measurement signal values of the test sensor units acquired during the plurality of calibration measurement sequences, the calibration model 120 may allow for, or may include, a prediction of a correlation between the baseline value and a behavior of the sensing unit for different concentrations of the target gas.

In examples, the gas sensing device 100 further comprises a further sensing unit 110' for sensing a further target gas. The test sensor units of the plurality of test sensor units may have the same types as the sensing unit and the further sensing unit 110'. The calibration data may include measurement signal values of the test sensor units acquired during a plurality of calibration measurement sequences in which the test sensor units of the plurality of test sensor units are exposed to a sequence of varying concentrations of at least one of the target gas and the further target gas. For example, in the calibration measurement sequences, the test sensor units of the plurality of test sensor units are exposed to a sequence of varying environmental conditions which are characterized at least by one or more of the environmental parameters, which may include at least one of the concentrations of the target gas and the further target gas.

The further sensing unit 110' may have a different sensitivity to the target gas than the sensing unit 110. In examples, the signal calibration unit 130 may be configured for determining the calibrated measurement value 132 based on the measurement signal 112 and a further measurement signal 112' provided by the further sensing unit 110'. Optionally, the signal calibration unit 130 may determine a further calibrated measurement value which represents the concentration of a further target gas in the environment of the gas sensing device 100. According to these examples, the calibration model 120 may further be based on calibration data of a plurality of test sensor units having the type of the further sensing unit 110'. In examples, the calibration model 120 is based on calibration data of a plurality of test gas sensing devices having the same type as the gas sensing device 100. That is, the test gas sensing devices may comprise the same types of sensing units as the gas sensing device 100.

Having the sensing unit 110 and the further sensing unit 110' allows for comparing the measurement signal 112 and the further measurement signal 112', for example by considering a cross-correlation of the measurement signal 112 and the further measurement signal 112'. Therefore, the calibrated measurement value 132 may be determined more accurately. Further, a comparison of the measurement signal 112 and the further measurement signal 112' allows to detect a malfunction of one of the sensing unit 110 and the further sensing unit 110'.

In examples, the gas sensing device 100 further comprises a data storage holding a baseline value, i.e. a baseline value for the sensing unit 110. The signal calibration unit 130 may use the baseline value for determining the calibrated measurement value 132.

The baseline value may serve as an input for the determination of the calibrated measurement value 132 using the calibration model 120. The baseline value of the sensing unit 110 may be measured of the manufacturing of the gas sensing device 100 for the sensing unit 110. In examples, the baseline value may be updated during operation of the gas sensing device 100. This example is advantageously implemented in combination with the feature that the calibration data for the calibration model 120 comprises baseline values of the test sensing units. Thus, the baseline value of the sensing unit 110 allows for a classification of the sensing unit 110 relative to the test sensing units, so that the calibration model 120 allows for an accurate prediction of the calibrated measurement value 132 based on the calibration data of the test sensing units. As the baseline value may be measured without exposing the sensing unit 110 to a specific concentration of the target gas, the measurement of the baseline value of the sensing unit 110 may be easy, fast and cost-efficient. Further, as it may be possible to predict a time period within which the concentration of the target gas in the environment of the gas sensing device 100 during operation is low or zero, it may be possible to update the baseline value, so that a change of a characteristic of the sensing unit 110 may be considered in the determination of the calibrated measurement value 132 without a recalibration of the sensing unit 110 under laboratory conditions.

Figure 2:
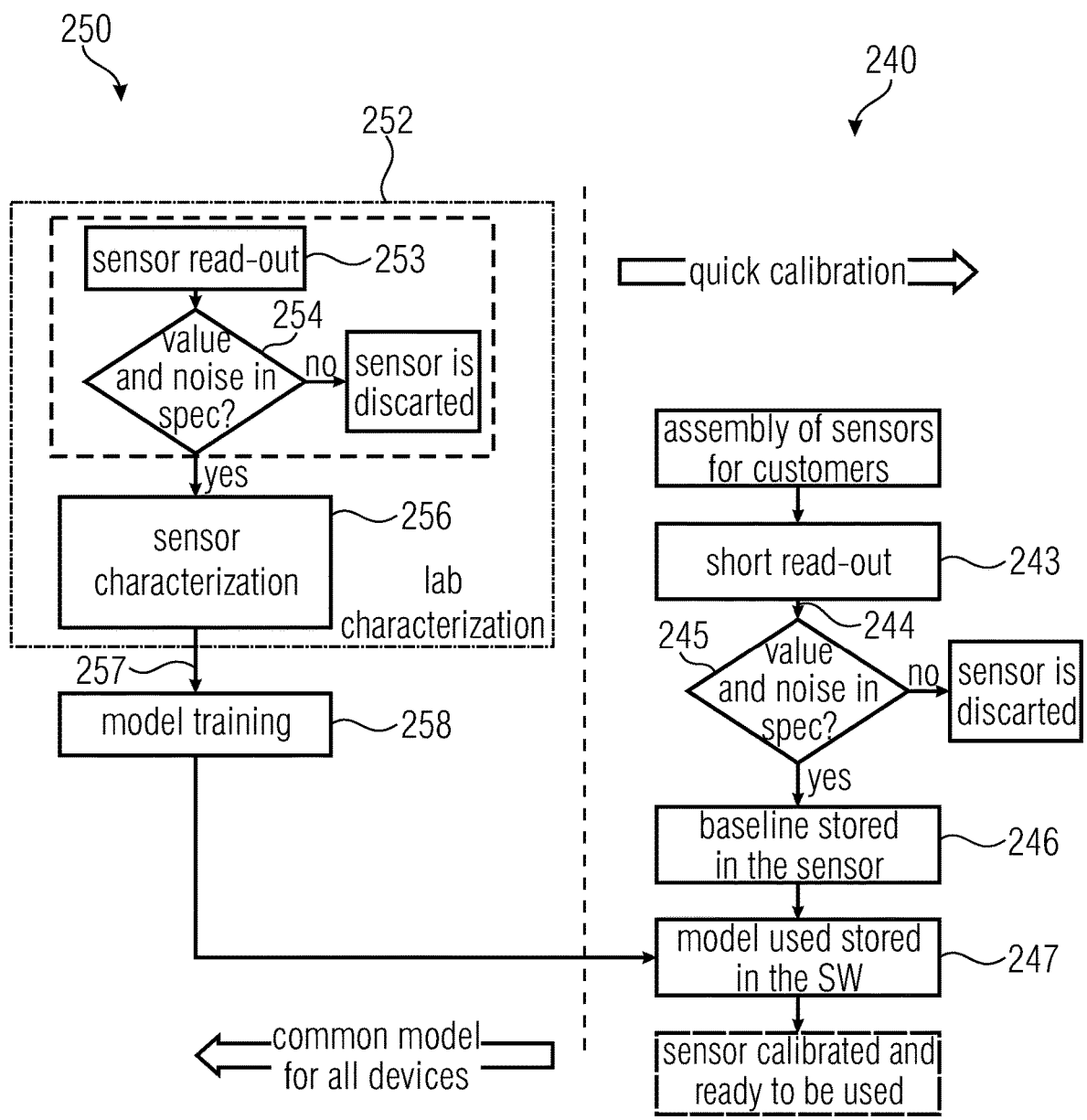
FIG. 2 illustrates an example of a method for obtaining the calibration model and an example of a method for calibrating the gas sensing device.

FIG. 2 illustrates an example of a method 250 for obtaining the calibration model 120 in combination with an example of a method 240 for calibrating the gas sensing device 100. The method 250 may represent a process to generate a common model, the calibration model 120, which model may be used for a plurality of gas sensing devices such as the gas sensing device 100. The method 240 may represent a quick calibration (e.g. just baseline) that is done on each of a plurality of manufactured gas sensing device. The methods 240 and 250 may be implemented independently from each other.

The method 250 comprises a characterization 252 of a test sensor unit. The characterization 252 comprises a step 253 of reading out the measurement signal of the test sensing unit, for example in a condition in which none of one or more of target gases of the test sensing unit is present in the environment of the test sensing units. That is, the baseline value of the test sensing unit may be measured. In a step 254 of the characterization 252, the measurement signal of the test sensing unit is evaluated with respect to one or more criteria, so as to decide whether the test sensing unit is to be used for determining the calibration model one 120 or not. For example, if the baseline of the test sensing unit is out of spec, for example higher or lower than a specific threshold, or if noise of the measurement signal of the test sensing unit is higher or lower than a specific threshold, the test sensing unit may be excluded from the determination of the calibration model 120. In other words, outliers of test sensing units may be excluded. It is noted that steps 253 and 254 are optional.

In a step 256 of the characterization 252, the test sensing unit is characterized, for example by exposing the test sensing unit to the plurality of calibration measurement sequences. For example, step 256 may include to acquire measurement signal values of the test sensing unit with and without background gases such as the target gas. For example, the calibration measurement sequences may be performed at different environmental conditions. The environmental condition for one of the calibration measurement sequences may be characterized by specific values of a set of environmental parameters, including one or more of the concentration of the target gas, temperature, relative humidity (RH), pressure, and further parameters. In examples, in step 256, a plurality of test sensing units, e.g. hundreds of test sensing units, may be characterized in parallel.

In other words, the test sensing units may be exposed to several realistic profiles of target gases (e.g. including the target gas and one or more further target gases of the gas sensing device 100) in known background conditions, e.g. synthetic air, and fixed humidity, temperature and pressure. Alternatively or additionally, the test sensing unit may be exposed to multiple realistic profiles including target gases and background gases (e.g. $NO_2$, $O_3$, CO, $SnO_2$, NO, $CH_4$ in the case of outdoor environment and $NH_3$, TVOCs, $CO_2$ in case of indoor environment). For example, the test sensing unit may be exposed to a respective realistic profiles of indoor environments and outdoor environments. A profile may refer to a temporal evolution of the concentration of one or more parameters such as the concentration of the target gas. Alternatively or additionally, the test sensing unit is exposed to one or more target gasses and different ambient temperatures and humidities. Alternatively or additionally, the test sensing unit is exposed to one or more target gasses and different (realistic) pressures.

The characterization 252 is performed for the plurality of test sensing units so as to obtain calibration data 257. In other words, a statistically relevant amount of samples (e.g. >100 devices) is characterized, for example by using a calibrated measurement set up. That is, for example concentrations of the target gas and further ambient conditions are known during the characterization procedure 252.

In a step 258 of the methods 250, the calibration model 120 is trained by using the calibration data of the plurality of test sensing units measured during step 256. Optionally, the baseline value measured in step 253 services an additional input for training the calibration model 120. In other words, the calibration data obtained in step 252 is used to train and to generate an average model which is able to predict the concentration of the target gases independently from small manufacturing variations. For example, a dimensionality of the calibration model 120 may depend on the amount of features being extracted by the various sensor fields of the device. For example, the sensor unit 110 and optional one or more further sensing units 110' may be referred to as sensor fields of the gas sensing device 100. The damage nullity of the calibration model 120 may further depend on a sampling time of the output and the number of target gases.

In other words, the method 250 is for building up a model of the response of the sensing unit 110 using supervised learning techniques, the model being robust against small manufacturing variations. Therefore, an individual calibration of the single chips, e.g. the sensing unit 110, with the target gases may not be required.

The method 240 for calibrating the gas sensing device 100 comprises a step 243 of reading out the measurement signal of the sensing unit 110, which may be performed after an assembly of the gas sensing device 100. Similar to step 253 of method 250, the step 243 may be performed in the absence of target gases in the environment of the gas sensing device 100. Thus, step 253 may yield the baseline value 244 of the sensing unit 110. In other words, of the assembly of a bit gas sensing unit, a short readout on the clean air may performed to measure the baseline of the sensor. In step 245, the baseline value 244 is evaluated with respect to one or more criteria so as to decide whether to discard the sensing unit are not. The criteria applied in step 245 may be same criteria as applied in step 254 of method 250. If the sensing unit 110 is not discarded, in step 246 the baseline value 244 is stored in the gas sensing device, e.g. on a data storage such as an ASIC of μC registers. In step 247, the calibration model 120 obtained by methods 250 is stored in the gas sensing device 100.

The common acquired model, that is the calibration model 120, may be stored in a firmware of the gas sensing device 100 and further gas sensing devices of the same type, and may be used by the firm that to predict the concentration of the target gases.

In examples, the baseline value 244 (or the sensor baseline) is the only sensor specific calibration data (i.e. the only calibration data obtained from the gas sensing device 100) which is needed for determining the calibrated measurement value 132 of the gas sensing device 100.

Calibrating the gas sensing device 100 using the methods 250 and 240 may drastically reduce the calibration cost since a single model may be used for a plurality of gas sensing devices like the gas sensing device 100. That means, that no individual calibration with different target gases and concentrations is required. Just a short read-out under synthetic air may be necessary. The cost of the calibration setup will be drastically lower (no mass flow controllers, pipes, gas bottles required, special room with adequate ventilation, etc.) and the cost of the calibration itself will decrease thanks to a shorter calibration time.

Figure 3:
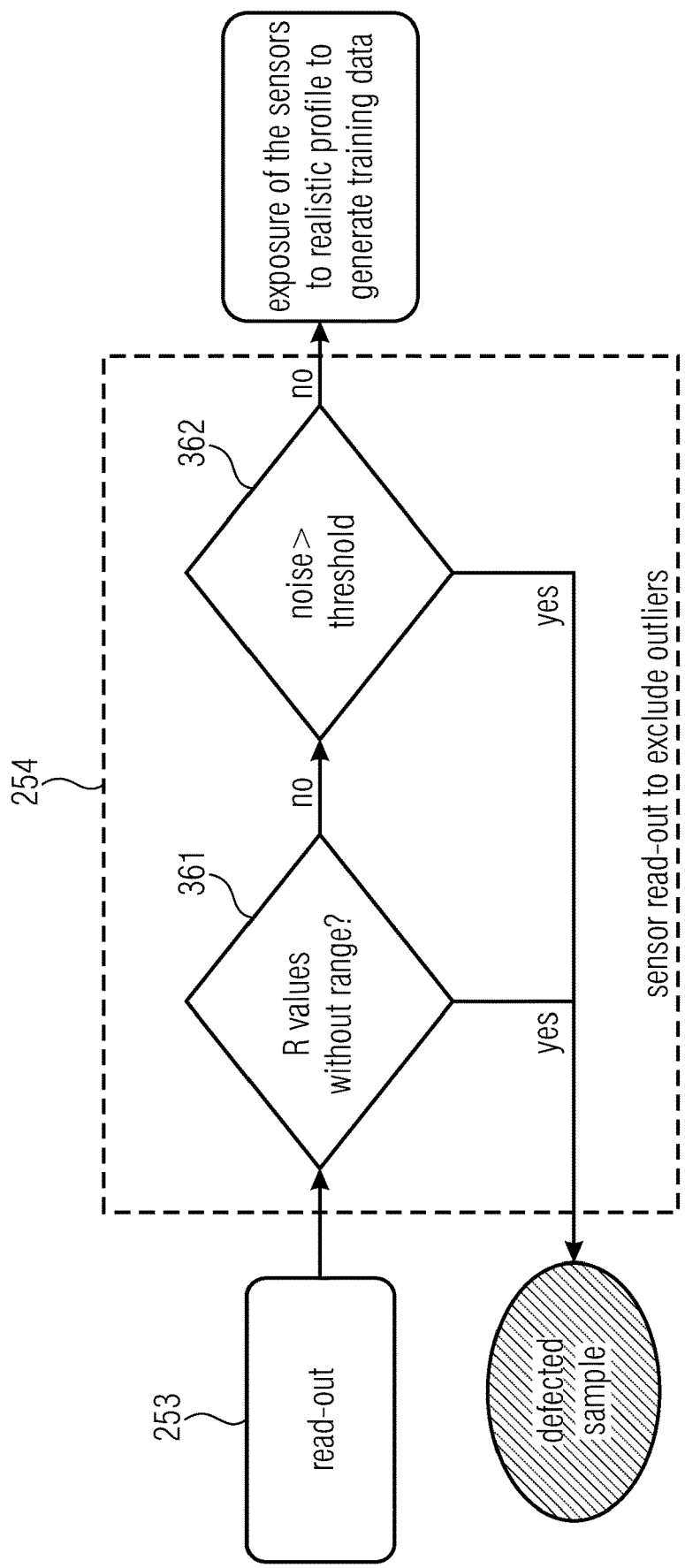
FIG. 3 illustrates an example of pre-selecting the test sensing units.

FIG. 3 illustrates an example of step 254 of evaluating the baseline of the test sensing units. For example, readout of the baseline values of the test sensing units in step 253 may be performed at a specific temperature such as 25° C. In a step 361, an R value of the measured baseline may be tested against a target value or against a target range. For example, it may be tested in step 361, whether the R value is within or without a specific target range. For example, a test sensing units may be regarded as defect, if the R value is higher or lower by more than a relative threshold, e.g. 20%, of a target value. In a step 362, a noise of the measured baseline may be compared to a target value. In examples, a test sensing unit may be regarded as defect, if the noise of the baseline exceeds a threshold, e.g. is more than 20% over a target value. If both steps 361 and 362 indicate that a test sensing unit is not defect, the test sensing unit may be used for generating calibration data for the calibration model 120. In other words, the board block diagram of FIG. 3 illustrates how outliers may be identified and excluded from the characterization in order to build a robust calibration model.

Figure 11A:
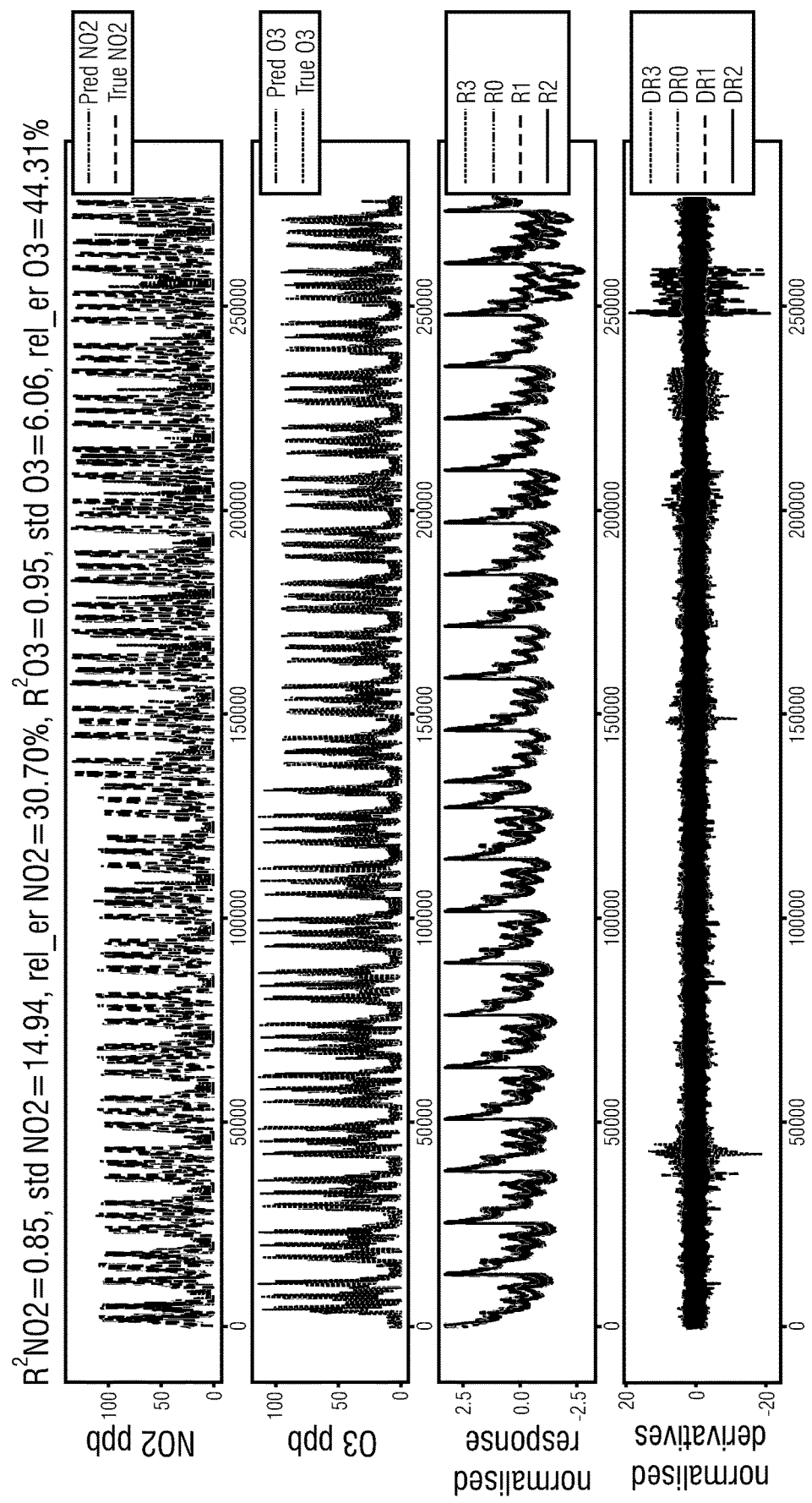
FIGS. 11A and 11B illustrate the accuracy of the calibration model according to an example.
Figure 11B:
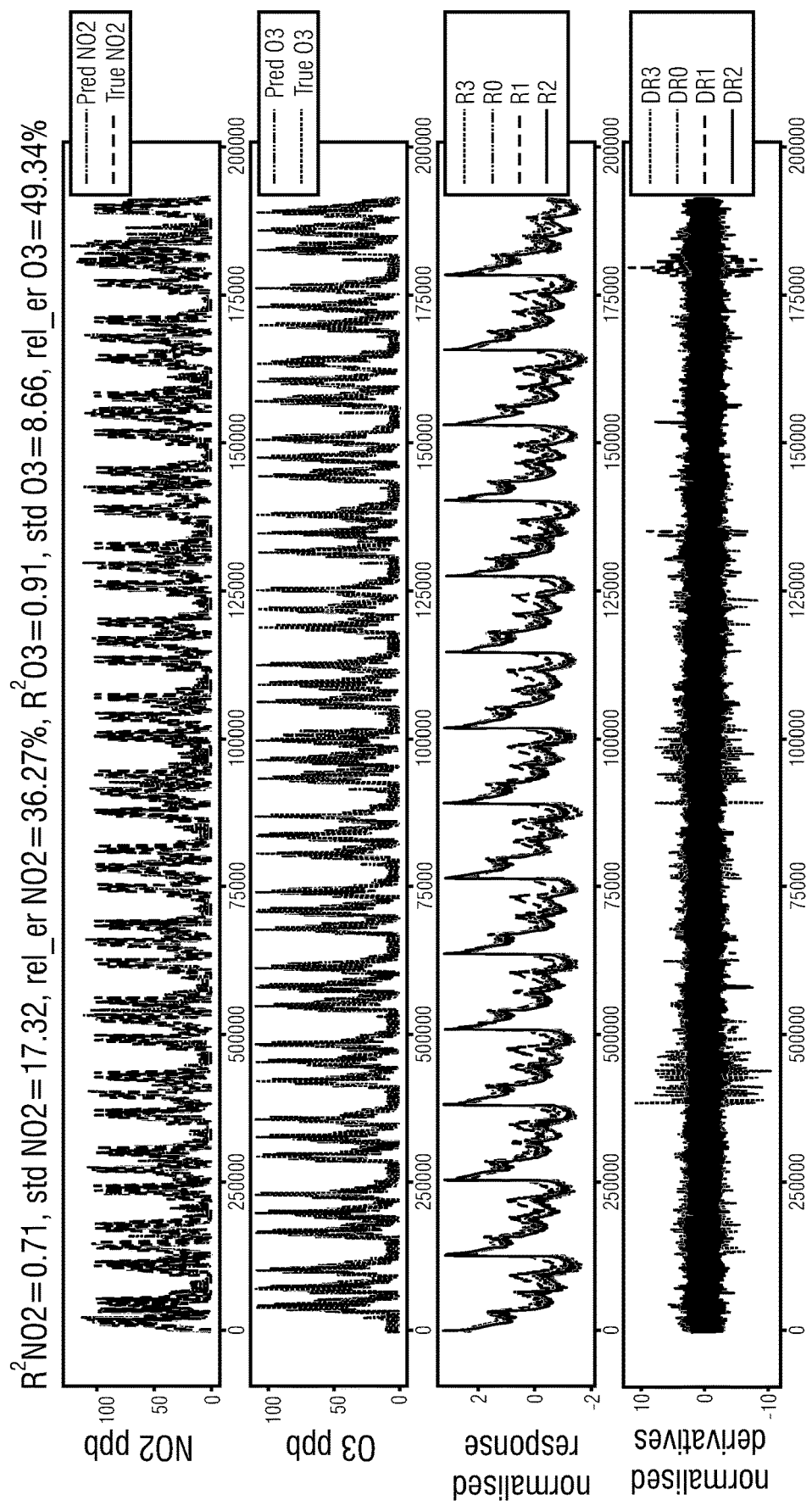

FIGS. 11A and 11B provide an example of how the calibration model 120 trained on a first group of sensing devices effectively generalizes to a second group of sensing devices, which has not been used for training the calibration model 120. FIG. 11A shows calibrated measurement values for the concentration of $NO_2$ and $O_3$ (Pred NO2, Pred O3) determined from measurement signals of the first group of sensing devices in comparison with concentrations of the respective gases (True NO2, True O3). FIG. 11B shows the corresponding data determined from measurement signals of the second group of sensing devices. Please note that sensors not in spec have been preliminary discarded according to the method in FIG. 2 and FIG. 3.

Continuing with the description of FIG. 1, in examples, the gas sensing device 100 further comprises means for determining an operational condition of the gas sensing device 100. Further, the gas sensor device 100 may comprise means for switching the calibration model in response to a change of the operational condition.

The means for determining the operational condition and the means for switching the calibration model may, for example, be provided by the means 134 which may optionally be part of the signal calibration unit 130 as indicated in FIG. 1. Alternatively, the means 134 may be separate means, e.g. comprising one or more of a signal processor, a communication interface, a sensing device.

The operational condition may include one or more of a malfunctioning of the sensing unit 110 and/or the further sensing unit 110', a geolocation of the gas sensing device 100, and an indication about whether the gas sensing device 100 is located indoor or outdoor. For example, the means 134 for determining the operational condition may comprise an interface for receiving an indication of the operational condition, such as the geolocation. The means 134 may be configured for determining the operational condition, e.g. by sensing the geolocation. In other examples, the means 134 for determining the operational condition may comprise a signal processor for evaluating the concentration of the target gas as determined by the gas sensing device 100. For example, based on a knowledge about typical concentration profiles of the target gas (i.e. an evolution of the concentration of the target gas over time), the gas sensing device 100 may infer the operational condition, such as the geolocation or the indoor/outdoor location. Also, the gas sensing device may infer a functional state of the sensing unit 110, 110' from the evaluation of the concentration of the target gas. E.g., the functional state may indicate whether the sensing unit 110 is malfunctioning. Switching the calibration model in response to a change of the operational condition, for example by selecting a calibration model which is representative of the operational condition of the gas sensing device 100, may ensure that the calibration model 120 is suitable for the operational condition of the gas sensing device 100. Thus, an accurate determination of the calibrated measurement value 132 may be granted even after a change of the operational condition.

In other words, examples of the disclosure may implement methods for ensuring long term validity of the acquired calibration model, the methods comprising one or more of (1) defect detection and elimination of malfunctioning sensors, (2) recalibration of the model as part of a maintenance or upgrade procedure, (3) a cleaning protocol to restore the sensor properties and thus preserve the sensitivity of the sensor and thus the validity of the acquired model over a longer period of time. These methods may be triggered by an internal mechanism of the gas sensing device 100 that collects internal statistics on the sensor signals (including the predictions from the estimation algorithm, i.e. the calibrated measurement values) and decides accordingly whether a different or improved calibration model is needed. Alternatively, if some form of (sporadic) connectivity to a monitoring station or similar device is available, then the additional information available (e.g. geographical data) from the external device could also be used to start the procedures (1)-(3). The examples of the gas sensing device 100 described in the following may optionally implement one or more of the method steps (1)-(3).

In examples, the gas sensing device 100 comprises a further sensing unit 110' for sensing a further target gas, the further sensing unit 110' being configured for providing a further measurement signal 112' based on a concentration of the further target gas in the environment of the gas sensing device 100. According to this example, the signal calibration unit 130 is configured for determining the calibrated measurement value 132 based on the measurement signal 112 and the further measurement signal 112'. Additionally, the gas sensing device 100 further comprises means for evaluating the further measurement signal 112' so as to decide whether the further sensing unit 110' is in a malfunctioning state. If the variation of the further measurement signal 112' indicates, that the further sensing unit 110' is in a malfunctioning state, the signal calibration unit 130 may determine the calibrated measurement value 132 independent of the further measurement signal 112'. Additionally or alternatively, if the evaluation of the further measurement signal 112' indicates, that the further sensing unit 110' is in a malfunctioning state, the signal calibration unit 130 may use, as the calibration model 120, a further calibration model which is independent of calibration data from test sensing units of the type of the further sensing unit 110'. Optionally, the means for evaluating the further measurement signal 112' may be provided by the means 134.

In other words, if the further sensing unit 110' is malfunctioning, the further measurement signal 112' may be excluded from the determination of the calibrated measurement value 132. Alternatively or additionally, the signal calibration unit 130 may switch the calibration model 120 and apply as the calibration model 120 a further calibration model. The further calibration model may be built such that it allows for a determination of the calibrated measurement value 132 independent of the further measurement signal 112'. For that purpose, the further calibration model is independent of calibration data of test sensing units of the type of the further sensing unit 110'. In other words, the further calibration model may be a reduced model which excludes the malfunctioning further sensing unit 110' from the determination of the calibrated measurement value 132. Thus, an outlying sensing unit may be eliminated from the determination of the calibrated measurement value 132. Determining the calibrated measurement signal 132 independent of the further measurement signal 112' and/or calibration data from test sensing units of the type of the further sensing unit 110' may allow for a reliable determination of the calibrated measurement value 132 in case of a malfunctioning of the further sensing unit 110'.

In other words, during the lifetime of a device malfunctioning can occur due to damage or defect. This can happen, for instance, if the sensing layer presents defects or damages, e.g. irregularities of the sensing layer or scratches in the sensing layers that are not detected during a characterization of the gas sensing device on wafer level (e.g. scratches cause during pre-assembly and assembly), or if the MEMS shows some defects, e.g. delamination of some metal lines or broken membranes, or if the bonding wires are damaged or the adhesion of the bond was poor (for instance due to surface contamination). In such cases, the sensor will either not respond or deliver values which are way above or below the expected ranges for the concentration ranges and dynamics the sensor has been calibrated for. For example, it may be tested whether the noise level of the raw signal, e.g. the measurement signal 112, is higher than the levels experienced in the lab. Additionally or alternatively, it may be tested whether one or both of the sensitivity and the derivative are lower or higher than the values experienced in the lab. For testing these criteria, the raw signal may be evaluated for a prolonged amount of time, e.g. over several days. These criteria may be used for testing a functional state of a sensing unit, that is to determine whether the tested sensing unit is malfunctioning or not.

Figure 4:
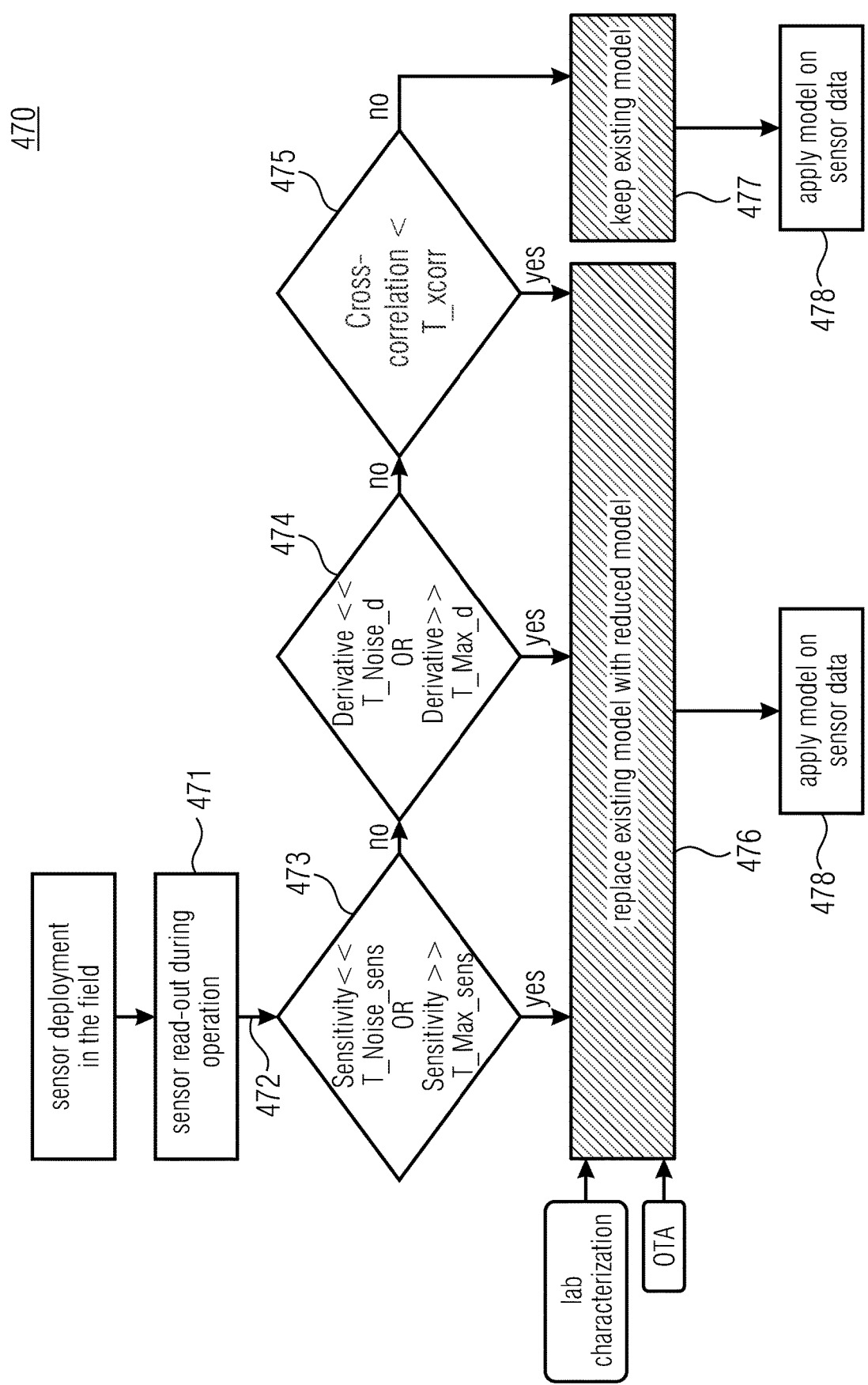
FIG. 4 illustrates an example of testing a functional state of the gas sensing device.

FIG. 4 illustrates a flowchart of an example of a method 470 for selecting a calibration model in dependence on a functional state of a tested sensing unit of the gas sensing device 100. Examples of the signal calibration unit 130 of FIG. 1 may perform method 470. During operation of the gas sensing device 100, the measurement signal of the tested sensing unit, e.g. the further sensing unit 110', is a read out in a step 471, so as to obtain measurement signal values 472.

In a step 473, the measurement signal values 472 are used for evaluating the sensitivity of the tested sensing unit, e.g. by testing the sensitivity with respect to one or more thresholds. In a step 474, the measurement signal values 472 are used for evaluating a derivative of the measurement signal or of the sensitivity of the measurement signal, e.g. by testing the derivative with respect to one or more thresholds. In step 475, a cross-correlation between the measurement signal of the tested sensing unit and one or more of the sensing units such as the sensing unit 110 is evaluated, e.g. the testing the cross-correlation against the one or more thresholds. The testing of the sensitivity in step 473, the derivative in step 474, and the cross-correlation in step 475 may, for example, be performed by using respective thresholds. For example, the sensitivity and its derivative and the noise level may be compared to pre-stored thresholds T_Noise_sens or T_Max_sens (for the sensitivity) and T_Noise_d and T_Max_d (for the derivative). Similarly, it has been observed that the presence of an interfering background gas can also cause a specific sensor field, i.e. sensor unit, to react to it more than the other fields and behave in an unexpected way. Since the responses from the sensor fields to various concentration events tend to be quite similar, monitoring the correlation among them over time provides an additional indicator on the status of the sensor. Sensor cross-correlation could be defined as $$R_s[r, p] = \frac{1}{n}\sum_{k=1}^{n} x_{i,r} x_{i,p}$$

where $x_r$ and $x_p$ indicate the normalized response at sensor r and p, respectively, at different moments in time and n is the window size being used to calculate the cross-correlation.

If any of the steps 473, 474, 475 indicates, that the tested sensing unit is malfunctioning, the method 470 may proceed with step 476 of replacing the calibration model 120 with a further calibration model, e.g. a reduced model. The reduced model may be obtained from calibration data measured under laboratory conditions, e.g. as described with respect to the method 250. For example, the reduced model may exclude calibration data of test sensing units of the type of the malfunctioning tested sensing unit. If none of the steps 473, 474, 475 indicates a malfunctioning of the tested sensing unit, the existing calibration model 120 may be kept, cf. step 477. In a step 478, the calibration model 120 may be used for determining the calibrated measurement value 132 on the basis of the measurement signal 112. Each of the steps 473, 474, 475 may be optional, so that the method for 70 may also be implemented without one or more of the steps 473, 474, 475. Further, in alternative implementations, the calibration model may be kept, if a selection, but not necessary all of the steps 473, 474, 475 do not indicate a malfunctioning of the test sensing unit. For example, step 476 is performed, if two or more of the steps 473, 474, 475 indicate a malfunctioning of the tested sensing unit.

The further calibration model on the reduced calibration model may be stored in a data storage and the gas sensing device 100 or may be provided to the gas sensing device 100 via a communication interface, for example over the air. For example, the gas sensing device 100 may be configured for requesting the further calibration model in response to the finding that the tested sensing unit, e.g. the further sensing unit 110', is malfunctioning.

In other words, according to examples, the original calibration model may be replaced with a reduced model which excludes the malfunctioning sensor fields and their related features. This reduced model could be pre-stored on the device memory or, if some form of connectivity is available even sporadically, a new model in memory can be transferred and stored on the device over the air (OTA).

Continuing in the description of FIG. 1, according to examples, the gas sensing device 100 further comprises means for obtaining information about a location, e.g. a geolocation or an indoor/outdoor location, of the gas sensing device 100. According to these examples, the signal calibration unit 130 is configured to use, as the calibration model 120 a calibration model which is based on calibration data which is representative of the location. Optionally, the means for obtaining information about the location may be provided by the means 134.

For example, the calibration data which is representative of the location may have been obtained by exposing the plurality of test sensing units to profiles, e.g. concentration profiles, which are characteristic are representative for the location.

For example, during operation, the gas sensing device 100 may obtain information on the geographic location of the gas sensing device 100 (e.g. urban or rural, latitude, altitude, etc.). A geolocation may be associated with specific characteristics of the gas profiles (or patterns), such as typical ranges for the concentration, dominant gases in the mixture, relative dynamics. For example, the typical range of concentration of the main pollutants may vary a lot from city to city, depending for instance on the population density, the local culture and habits.

Figure 5A:
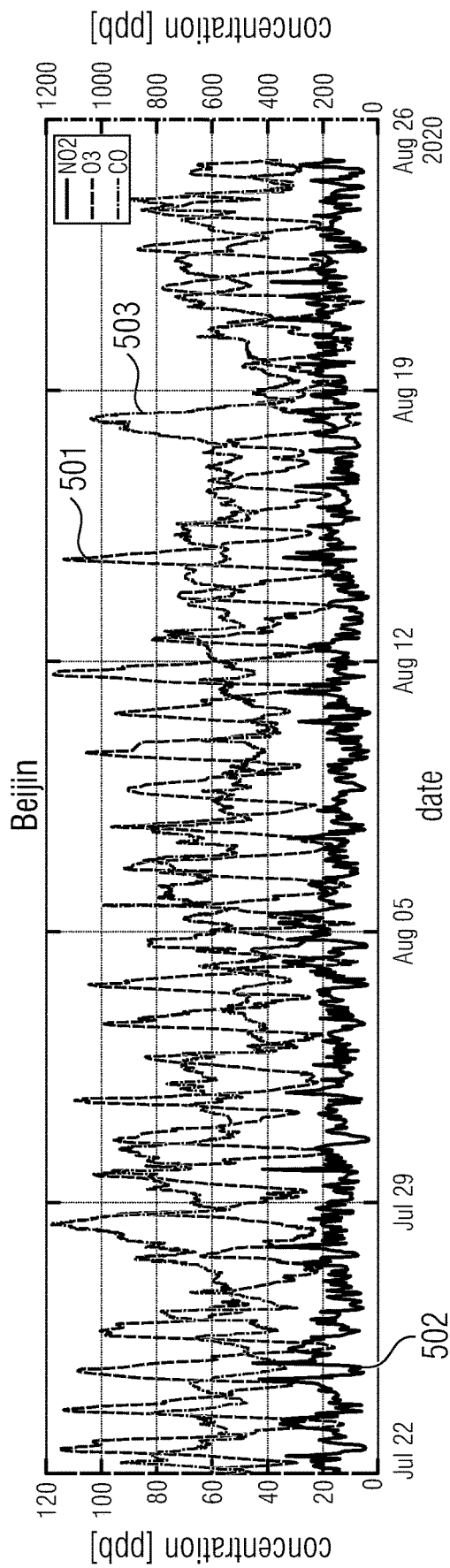
FIGS. 5A, 5B, and 5C show examples of concentration profiles of $NO_2$ and $O_3$.
Figure 5B:
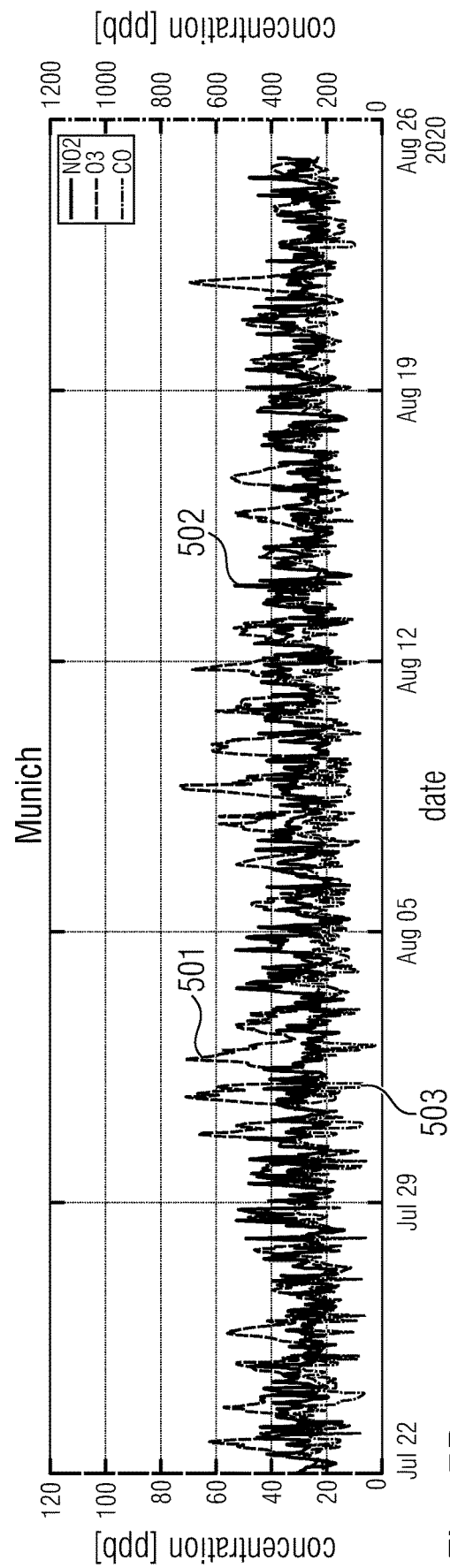
Figure 5C:
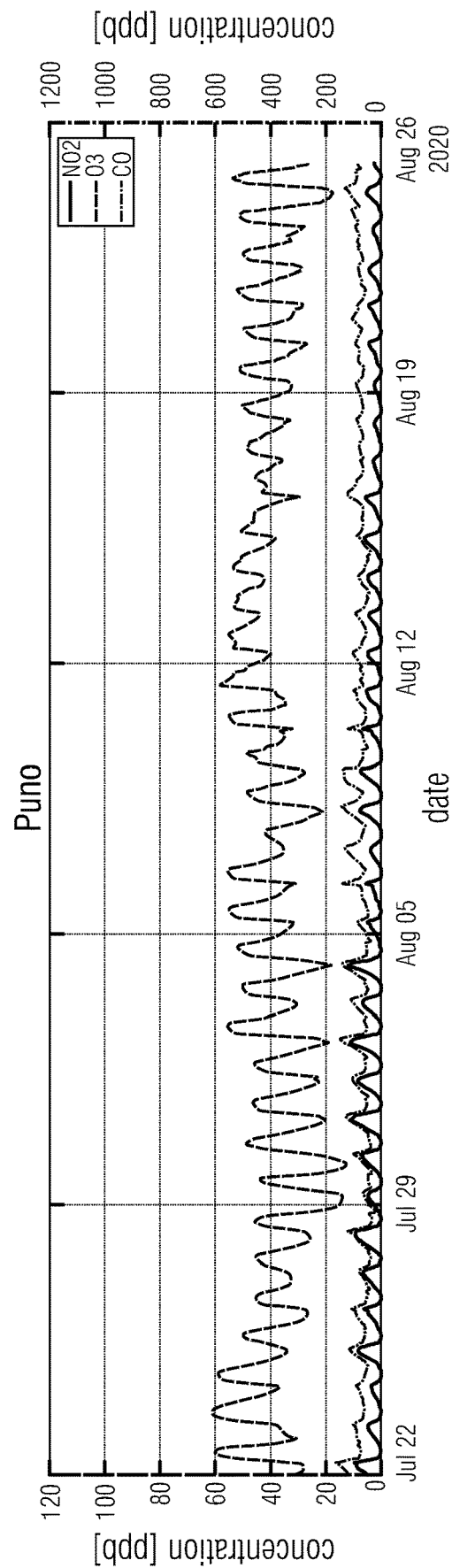
Figure 6A:
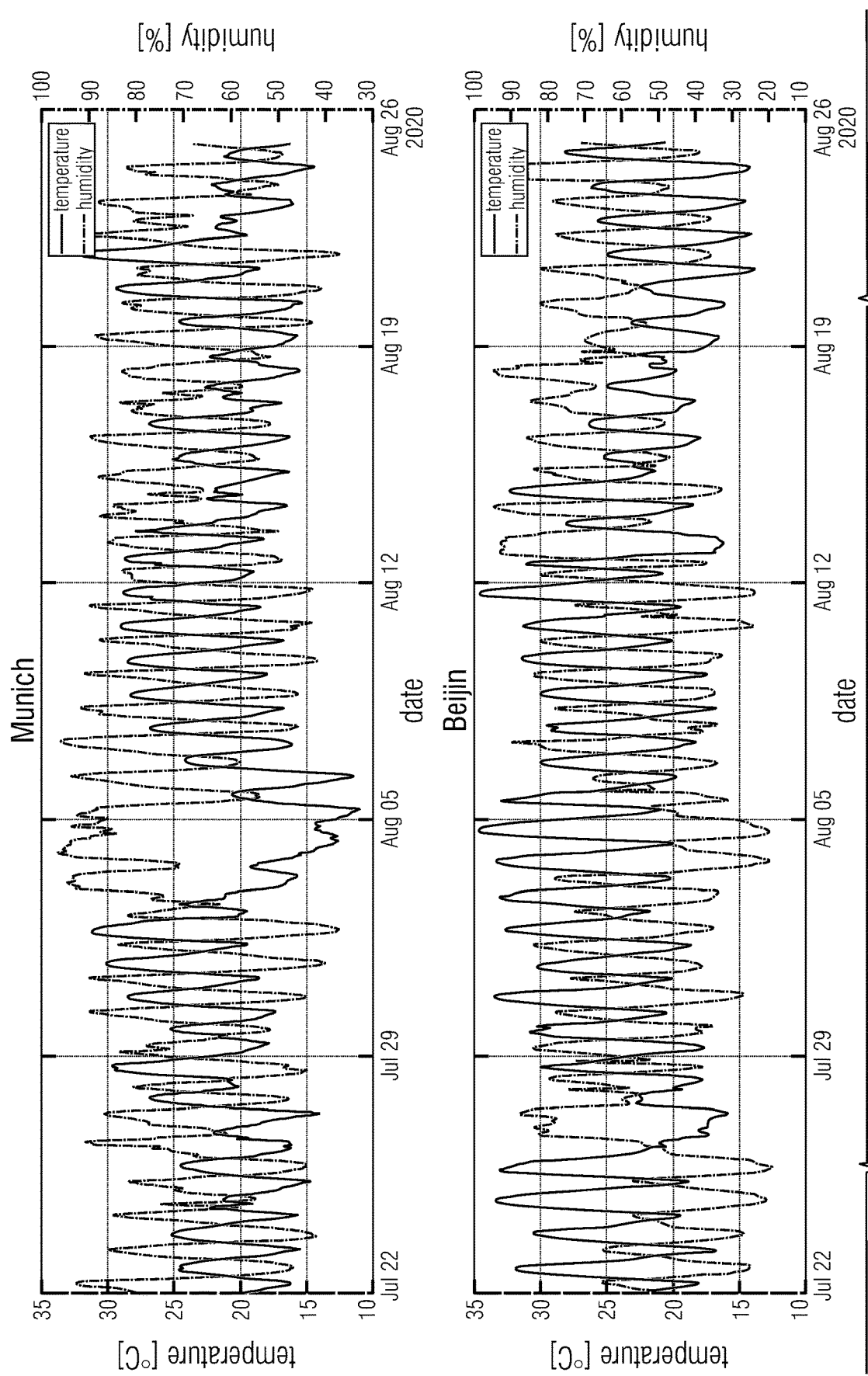
FIGS. 6A and 6B show examples of temperature and humidity profiles.
Figure 6B:
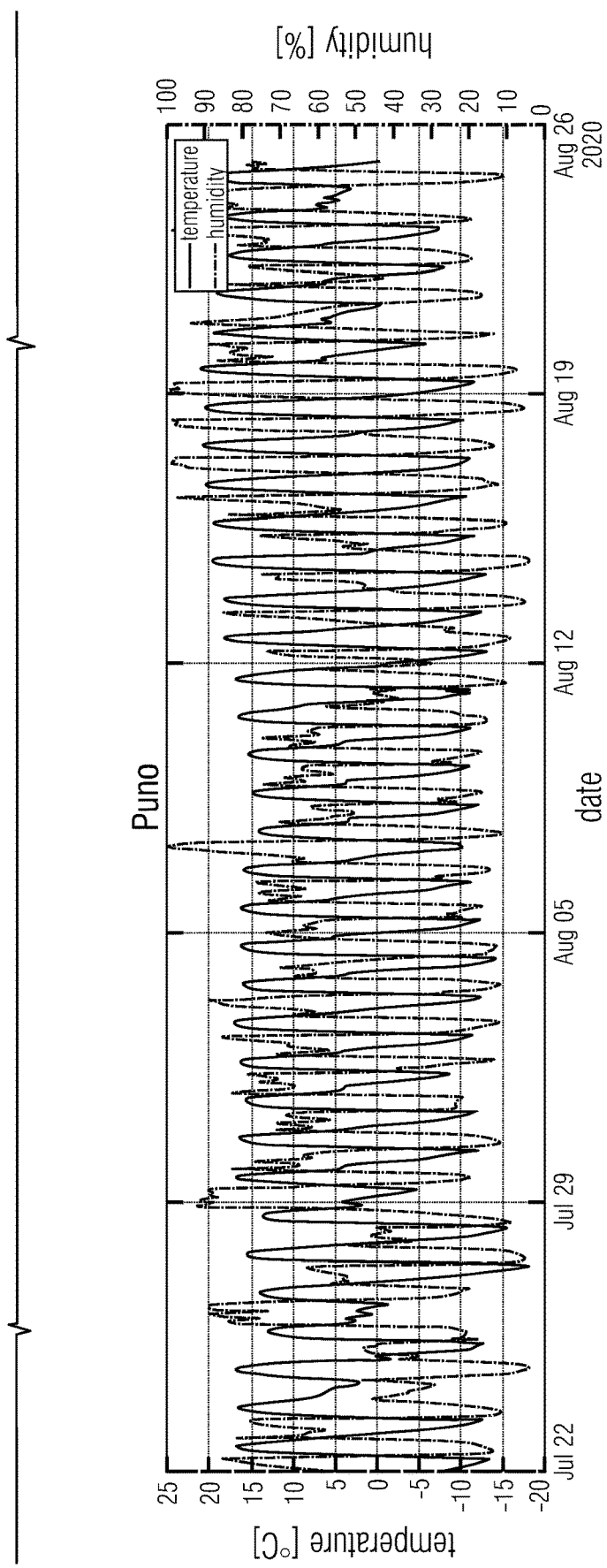

FIGS. 5A, 5B, and 5C show exemplary plots of the $NO_2$ concentration 502, the $O_3$ concentration 501 and the CO concentration 503 (in ppb) monitored for five weeks in three different cities: Beijing (FIG. 5A), Munich (FIG. 5B), and Puno (FIG. 5C). It can be observed from the graphs that in Beijing there are peaks of $O_3$ up to 120 ppb, while the $NO_2$ concentration didn't increase more than 40 ppb during the monitoring period. The CO levels in the same cities reached peaks of 1200 ppb. In Munich, on the other side, the variation of $NO_2$ and $O_3$ were shift to lower concentrations, with maximum values around 70 ppb for $O_3$ and 50 ppb for $NO_2$ and CO concentration below 300 ppb. If we look at smaller cities with very low population density, like Puno, we see that the range for $NO_2$ is even more compressed (with maximum values of 10 ppb) and maximum values for $O_3$ below 60 ppb, the CO concentration is below 200 ppb. Additionally, the temperature and relative humidity can also vary a lot from region to region. An example of temperature and relative humidity for five weeks in Munich, Beijing and Puno are shown in FIGS. 6A and 6B.

In examples, the signal calibration unit 130 may select the calibration model 120 out of a plurality of calibration models, representing the differences and the different range of pollutants described exemplarily by FIGS. 5A-5C and FIGS. 6A-6B, e.g. one calibration model to predict the target gas concentrations in big cities in Asia, a second calibration model to predict the gas concentration in big cities in Europe, a third calibration model for cities with very low population density or countryside. Selecting a calibration model according to the geolocation of the gas sensing device 100 may improve the accuracy in the determination of the calibrated measurement value 132.

In other words, the existing pre-defined model, e.g. the calibration model 120 stored in the gas sensing device after manufacturing, may be replaced by a new one (the further calibration model), which may be the result of a more accurate training process where the additional information on the gas behavior has been accounted for. For example, this new model could be transferred over the air to the device, if some sporadic connectivity is available, or it could be activated from an already available pool of models stored in memory once the geographic location or the specific characteristics of the patterns are identified.

In examples, the gas sensing device 100 comprises means for characterizing an environment of the gas sensing device 100 by evaluating an evolution, e.g. a temporal evolution, of the measurement signal 112 during a period of time. The signal calibration unit 130 may be configured to select, as the calibration model 120, a calibration model on the basis of the characterization of the environment of the gas sensing device 100. Optionally, the means for characterizing the environment of the gas sensing device may be provided by the means 134.

In other words, the sensor algorithm could also keep track of the gas estimates (e.g. ranges and rate of variation) over a certain period of time and select a more accurate model with better matched gas concentration ranges.

Figure 7:
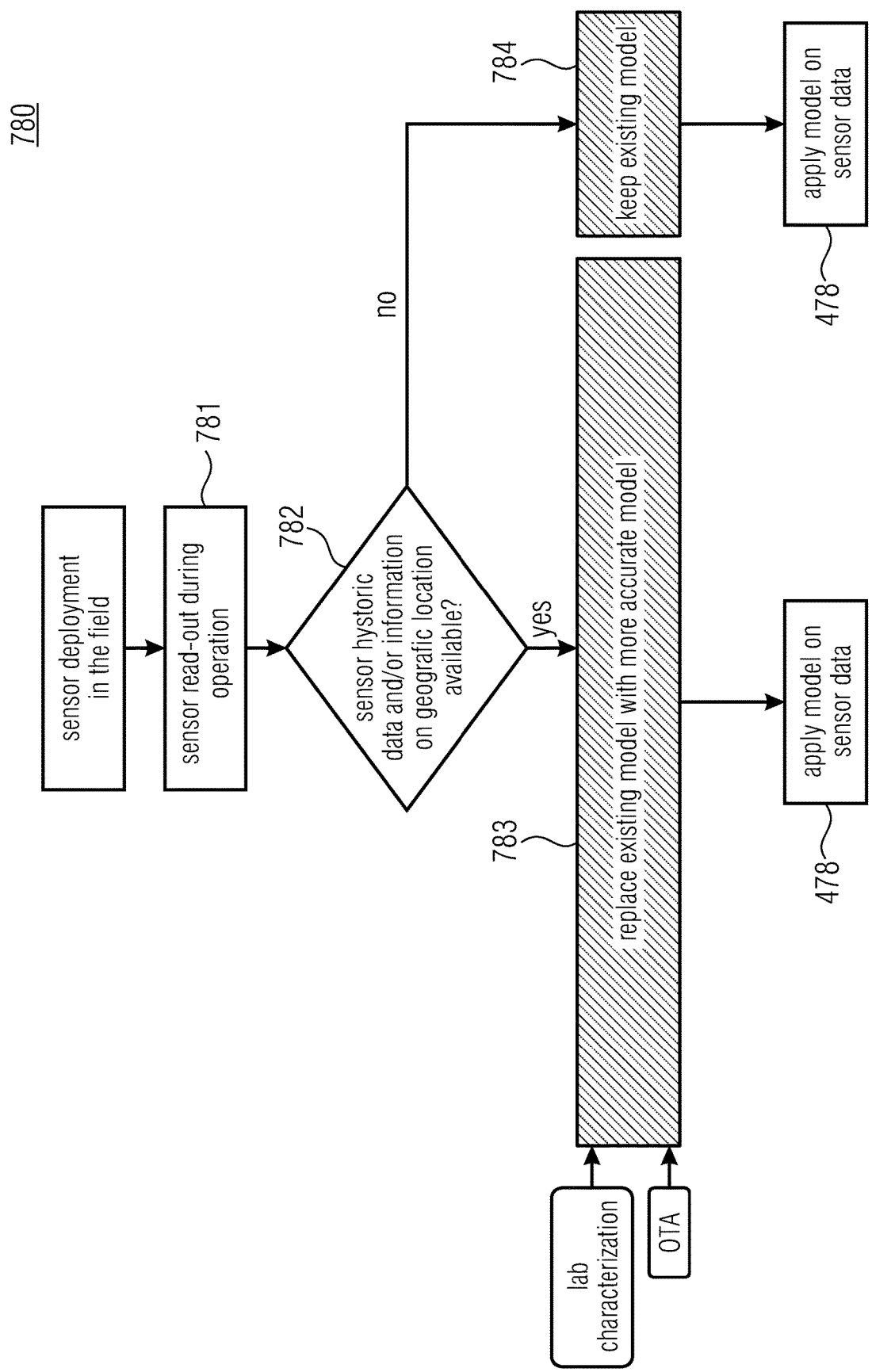
FIG. 7 illustrates an example of evaluating an operational condition of the gas sensing device.

FIG. 7 shows a flow chart of an example for a method 780 for selecting the calibration model 120 in dependence on the location of the gas sensing device 100 and/or in dependence on an evolution of the measurement signal 112. For example, the method 718 may be performed by the signal calibration unit 130 of FIG. 1. During operation of the gas sensing device 100, in step 781 of the method 780, the measurement signal 112 is acquired. In step 782 of the method 780, the evolution of the acquired measurement signal 112 is compared with historic data, for example with data every presenting evolution of the measurement signal 112 in earlier time period. Thus, a change of the sensor characteristics may be detected, and a type of the change of the sensor characteristics may be classified, so as to select a suitable calibration model. Alternatively or additionally, in step 782, and information on the location, e.g. a geographic location, of the gas sensing device 100 is used for selecting a calibration model. Alternatively or additionally, in step 782, and evolution of the measurement signal 112 is evaluated so as to characterize the environment of the gas sensing device 100. Subsequently, a calibration model which matches the environment of the gas sensing device 100 may be selected. If an information about the location of the gas sensing device 100 is available, or if historic data is available, in step 783 the calibration model 120 may be replaced with a more accurate calibration model, for example a calibration model which better matches the operational condition of the gas sensing device 100. If no better matching calibration model is available, or if no information on the location and/or historic data and/or information on possible environment of the gas sensing device 100 is available, step 784 of keeping the currently used calibration model may be performed.

In examples, the gas sensing device 100 comprises means 136 for receiving a further calibration model 120' and the signal calibration unit 130 is configured to use the further calibration model 120' as the calibration model 120.

For example, the means 136 for receiving the further calibration model include a communication interface. The further calibration model 120' may provide for any of the calibration models to which the gas sensing unit 110 may switch in response to the operational condition. Having the means for receiving the further calibration model allows for adapting the calibration model 120 according to the operational condition of the gas sensing device 100, for example according to the functional state of the sensing unit 110, according to the location of the gas sensing device 100 or according to an evolution of the concentration of the target gas as described with respect to FIG. 4 to FIG. 7, without imposing higher requirements regarding memory capacity on the gas sensing device 100.

According to further examples, the gas sensing device comprises a data storage 138 holding a plurality of calibration models. According to this example, the signal calibration unit 130 is configured to select the calibration model 120 for the determination of the calibrated measurement value 132 from the plurality of calibration models.

The plurality of calibration models may provide the calibration model to which the gas sensing device 100 may switch in response to the operational condition. Having the plurality of calibration models stored in the gas sensing device 100 has the advantage, that the calibration model 120 may be adapted even if the gas sensing device 100 has no connectivity, e.g. to a server. Thus, a reliable operation of the gas sensing device may be granted.

Figure 8:
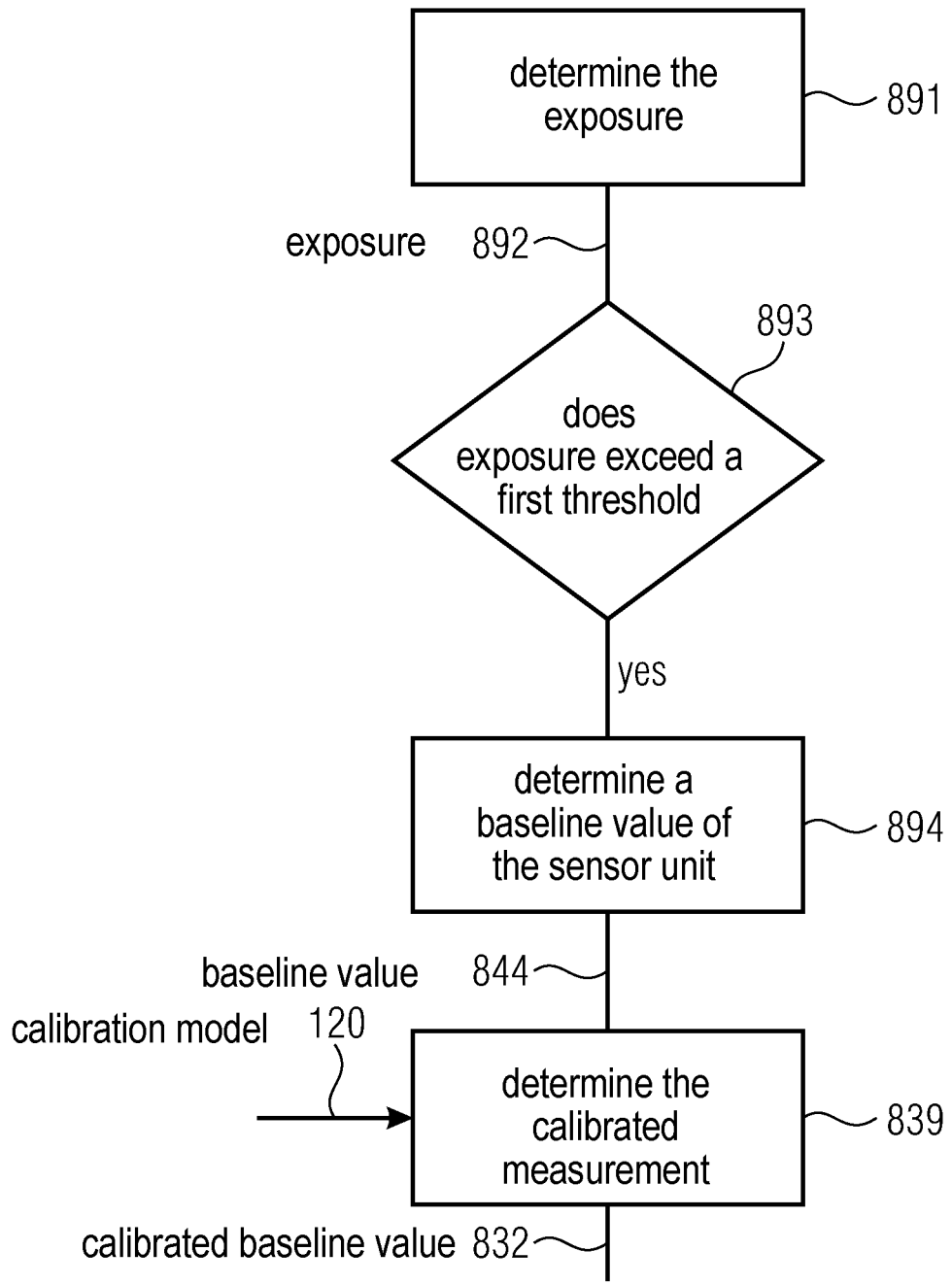
FIG. 8 illustrates an example for re-determining a baseline value of the sending unit.

FIG. 8 shows a block diagram of an example of an operation scheme 890, which may be executed by the gas sensing device 100, for example the signal calibration unit 130 of FIG. 1. According to this example, the gas sensing device 100 comprises means, e.g. the signal calibration unit 130, for detecting, in a step 893, whether an exposure 892 of the sensor unit 110 to the target gas exceeds a first threshold. Further, the gas sensing device 100 may comprise means for determining, in a step 894, a baseline value 844 of the sensing unit 110 if the exposure of the sensor unit 110 to the target gas exceeds the first threshold. According to this example, the signal calibration unit 130 is configured to use the determined baseline value 844 as an input for the calibration model 120 so as to determine, in a step 839, the calibrated measurement value 132.

For example, during operation of the gas sensing device 100, molecules of the target gas, e.g. $O_3$ or $NO_2$, may be adsorbed at the sensing unit 110. As described above, adsorbed gas molecules may decrease the sensitivity of the sensing unit 110, such changing the state of the sensing unit 110. The exposure 892 to the target gas may be an indication for an amount of the adsorbed gas molecules at the sensing unit 110.

Optionally, the operation scheme 890 comprises a step 890 one of determining the exposure 892 of the sensor unit to the target gas. The exposure 892 may be a measure for a concentration of the target gas to which the sensor unit 110 is exposed, for example during a specific period of time. For example, the exposure 892 may be determined by evaluating the measurement signal 112 or a plurality of calibrated measurement values 132 determined during a period of time, starting for example after a startup of the gas sensing device 100 or after a cleaning of the sensing unit 110. For example, the exposure 892 may be determined by integrating the concentration of the target gas over time.

The baseline value 844 may be determined as described with respect to the baseline value 244 of FIG. 2. For example, the baseline value 844 may be used to replace the baseline value 244 determined after manufacturing, or may be used for replacing a currently used baseline value. As described with respect to FIG. 2, the baseline value may be in indicator for classifying the sensing unit 110 with respect to the plurality of test sensing units. Thus, updating the baseline value allows for adapting the determination of the calibrated measurement value 132 to a current state of the sensing unit 110. Thus, a high reliability of the determination of the calibrated measurement value 132 in situations in which the state of the sensing unit 110 changes may be achieved.

In other words, as mentioned above, it can happen that during operation the sensor properties change in a reversible manner, for example when this is exposed to large concentration of gases such as O3 which are not quickly desorbed thus masking the presence of other gases (such as NO2) and hinder their accurate estimation. For a relatively low amount of adsorbed molecules, the molecules may be desorbed from the sensing unit 110 by heating the sensing unit 110, as will be described with respect to FIG. 9, such restoring an original state of the sensing unit 110. In the case in which a long exposure of the sensor to high concentration of $NO_2$ and $O_3$ is detected, a complete sensor recovery might not be possible. Under these circumstances the sensing unit may be recalibrated using a local baseline (i.e. determining the baseline value 844). For example, the baseline value 844 may be determined during a time when minimum concentration of $NO_2$ and $O_3$ are detected (this could typically happen around 5 a.m.). In this way an overestimation of the gas concentration can be avoided.

Figure 9:
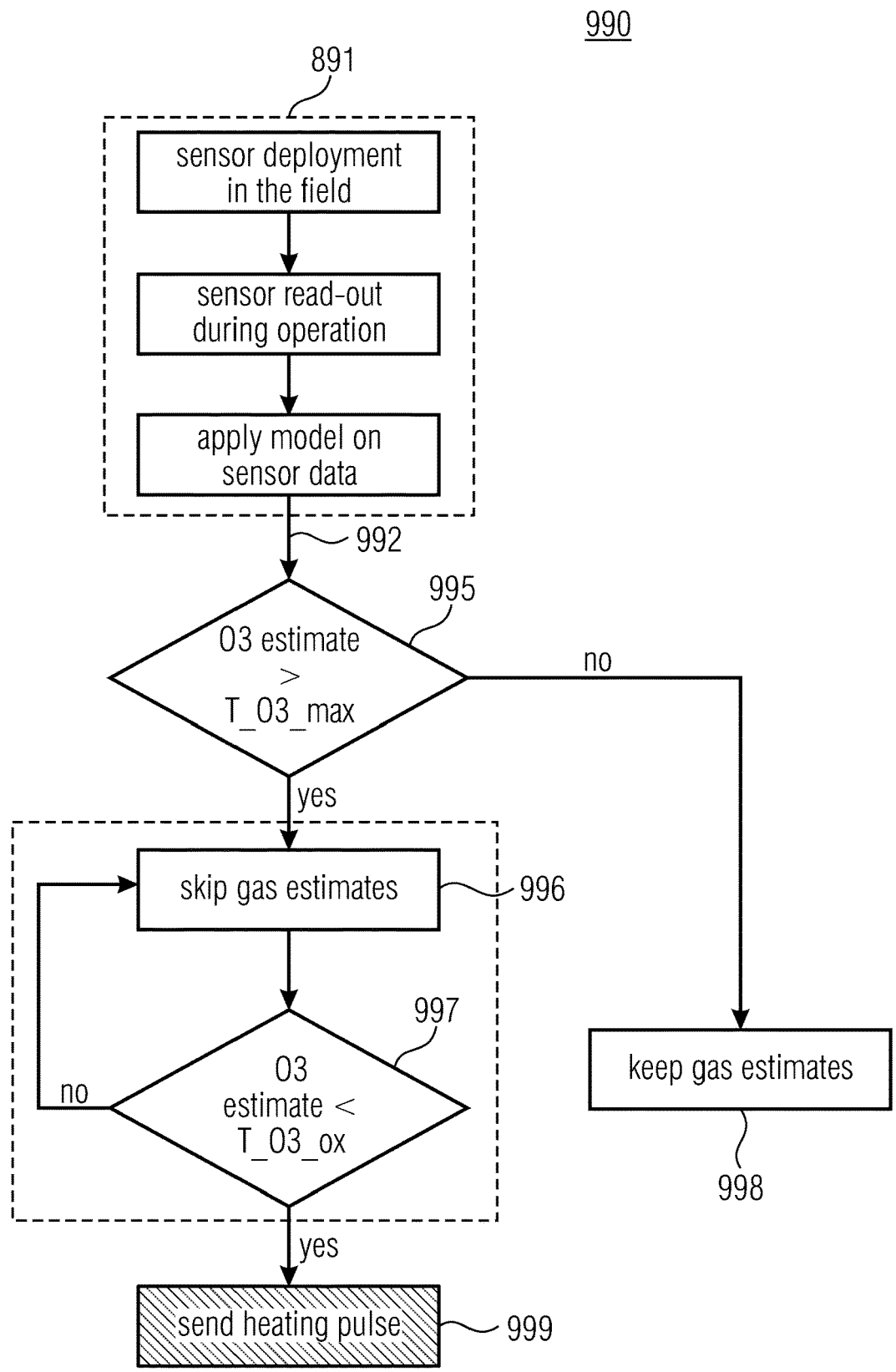
FIG. 9 illustrates an example for initializing a recovery sequence.

FIG. 9 shows a block diagram of an example of an operation scheme 990 which may be executed by the gas sensing device 100, for example by the signal calibration unit 130 of FIG. 1. According to this example, the gas sensing device 100 comprises means for detecting, in a step 995, whether an exposure 992 of the gas sensing device 100 to the target gas exceeds a second threshold. The gas sensing device 100 may further comprising means for initializing a recovery sequence 999, if the exposure of the gas sensing device to the target gas exceeds the second threshold.

The exposure 992 to the target gas may be determined according to the exposure 982 to the target gas. The recovery sequence 999 may comprise a heating of the sending unit 110 or of a sensing layer of the sensing unit 110. By heating the sensing unit 110, molecules may be desorbed from the sensing unit 110. In other words, the recovery sequence may clean the sensing unit 110, for example with a short heating pulse at very high temperature (e.g. >200° C.). The heating pulse may enhance the desorption of gas molecules, restoring the original sensitivity of the sensor so that the existing acquired model can be further used. Thus, the operation scheme 890 and the operation scheme 990 of FIG. 8 and FIG. 9 may be combined. For example, the second threshold may be lower than the first threshold. Thus, for a relatively low exposure to the target gas, exceeding the second threshold, the recovery sequence 999 may be performed, and for a relatively high exposure to the target gas, exceeding the first threshold, the baseline value may be re-determined.

Optionally, the operation scheme 990 comprises the step 891 of determining the exposure 992. Step 891 may comprise a readout of the measurement signal 112 and a determination of a plurality of calibrated measurement values 132 based on the measurement signal 112.

Optionally, the operation scheme 990 comprises a step 997 of determining whether the exposure 992 of the sensing unit 110 to the target gas is below a third threshold. Step 979 may be performed, if step 995 indicates that the exposure 992 is above the second threshold. Performing the recovery sequence 999 may result in a degradation of the sensing layer of the sensing unit 110, if the concentration of a specific gas, for example $O_3$, which may be the target gas, is high. Thus, the gas sensing device 100 may be configured to initialize the recovery sequence 999 if the exposure 992 exceeds the second threshold and is below the third threshold. In other words, the decision on when to trigger the recovery sequence 999, may be based on the estimate of the dominant gas provided by the algorithm, i.e. an indication for the exposure 992 to the target gas. For instance, after a high $O_3$ concentration is detected (>T_O3_mx), the estimates of the other gases are suspended until the estimated concentration goes down to a known value (T_O3_ox) at which it is possible to heat the sensor without damaging it.

Optionally, if step 995 indicates, that the exposure 992 is above the second threshold, the calibrated measurement value 132 is discarded or skipped, as indicated by step 996. Otherwise the calibrated measurement value 132 may be kept. For a high exposure 992, the concentration of the target gas may be overestimated by the calibrated measurement value 132. Thus, discarding the calibrated measurement value 132 in this case grants a reliable output of the gas sensing device 100.

Figure 10:
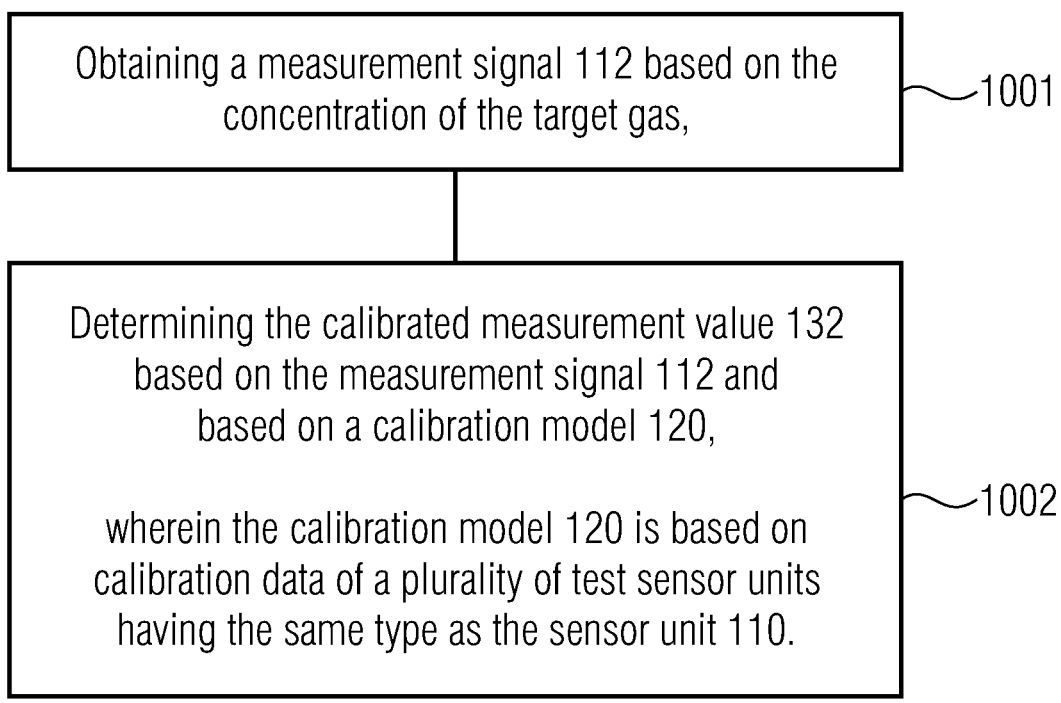
FIG. 10 illustrates a flowchart of an example of a method for obtaining a calibrated measurement value of the gas sensing device.

FIG. 10 shows a flowchart of an example of a method 1000 for determining a calibrated measurement value 132 for a concentration of the target gas. The method 1000 comprises a step 1001 of obtaining a measurement signal 112 based on the concentration of the target gas. The method 100 further comprises a step 1002 of determining the calibrated measurement value 132 based on the measurement signal 112 and based on a calibration model 120, wherein the calibration model 120 is based on calibration data of a plurality of test sensor units having the same type as the sensor unit 110.

In the following, further examples of the disclosure are described.

An example according to the disclosure provides a gas sensing device 100 for sensing a target gas, comprising:
- a sensing unit 110 for sensing the target gas, the sensing unit being configured for providing a measurement signal 112 based on a concentration of the target gas in an environment of the gas sensing device 100,
- a signal calibration unit 130, configured for determining a calibrated measurement value 132 based on the measurement signal 112 and based on a calibration model 120,
- wherein the calibration model 120 is based on calibration data of a plurality of test sensor units having the same type as the sensor unit.

According to an example, the calibration data 257 includes measurement signal values of the test sensor units acquired during a plurality of calibration measurement sequences in which test sensor units of the plurality of test sensor units are exposed 256 to a sequence of varying environmental conditions, wherein the environmental conditions are characterized at least by one or more environmental parameters including a concentration of the target gas.

According to an example, the calibration model 120 is a statistical model which is trained 258 by supervised learning techniques using the calibration data 257.

According to an example, the calibration data 257 of the test sensor units includes respective baseline values of the test sensor units.

According to an example, the gas sensing device 100 comprises a further sensing unit for sensing a further target gas, and the test sensor units of the plurality of test sensor units have the same types as the sensing unit and the further sensing unit. Further, the calibration data 257 includes measurement signal values of the test sensor units acquired during a plurality of calibration measurement sequences in which the test sensor units of the plurality of test sensor units are exposed 256 to a sequence of varying concentrations of at least one of the target gas and the further target gas.

According to an example, the gas sensing device 100 further comprises a data storage holding a baseline value 244, and wherein the signal calibration unit 130 is configured for using the baseline value 244 for determining the calibrated measurement value 132.

According to an example, the gas sensing device 100 further comprises:
  means for determining an operational condition of the gas sensing device 100, and
  means for switching the calibration model 120 in response to a change of the operational condition.

According to an example, the gas sensing device 100 comprises a further sensing unit 110' for sensing a further target gas, the further sensing unit being configured for providing a further measurement signal 112' based on a concentration of the further target gas in the environment of the gas sensing device 100, wherein the signal calibration unit is configured for determining the calibrated measurement value 132 based on the measurement signal 112 and the further measurement signal 112', and wherein the gas sensing device 100 further comprises:
  means for evaluating 472, 473, 474 the further measurement signal 112' so as to decide whether the further sensing unit 110' is in a malfunctioning state,
  and the signal calibration unit 130 is configured for, if the evaluation of the further measurement signal indicates, that the further sensing unit is in a malfunctioning state,
  determining the calibrated measurement value 132 independent of the further measurement signal, and/or
  using 476, as the calibration model 120, a further calibration model which is independent of calibration data from test sensing units of the type of the further sensing unit.

According to an example, the gas sensing device 100 further comprises means for obtaining an information about a location of the gas sensing device 100,
and the signal calibration unit 130 is configured to use 478, as the calibration model 120, a calibration model which is based on calibration data which is representative of the location.

According to an example, the gas sensing device 100 further comprises means for characterizing an environment of the gas sensing device 100 by evaluating an evolution of the measurement signal during a period of time,
and the signal calibration unit 130 is configured to select, as the calibration model 120, a calibration model on the basis of the characterization of the environment of the gas sensing device 100.

According to an example, the gas sensing device 100 further comprises means 136 for receiving a further calibration model, and wherein the signal calibration unit is configured to use the further calibration model as the calibration model.

According to an example, the gas sensing device 100 further comprises a data storage 138 holding a plurality of calibration models, wherein the signal calibration unit is configured to select the calibration model for the determination of the calibrated measurement value 132 from the plurality of calibration models.

According to an example, the gas sensing device 100 further comprises means for detecting 893 whether an exposure of the sensor unit to the target gas exceeds a first threshold, and
means for determining 894 a baseline value of the sensing unit if the exposure of the sensor unit to the target gas exceeds the first threshold, and
the signal calibration unit 130 is configured to use the determined baseline value as an input for the calibration model so as to determine the calibrated measurement value 132.

According to an example, the gas sensing device 100 further comprises means for detecting 995 whether an exposure of the gas sensing device 100 to the target gas exceeds a second threshold, and
the gas sensing device 100 comprises means for initializing a recovery sequence 999, if the exposure of the gas sensing device 100 to the target gas exceeds the second threshold.

According to an example, the gas sensing device 100 is a chemoresistive gas sensing device.

A further example of the disclosure provides a method 1000 for determining a calibrated measurement value 132 for a concentration of a target gas, the method comprising:
  obtaining 1001 a measurement signal 112 based on the concentration of the target gas,
  determining 1002 the calibrated measurement value 132 based on the measurement signal 112 and based on a calibration model 120,
  wherein the calibration model 120 is based on calibration data of a plurality of test sensor units having the same type as the sensor unit 110.

According to an example, the test sensor units of the plurality of test sensor units have the same types as the sensing unit and a further sensing unit, and the calibration data 257 includes measurement signal values of the test sensor units acquired during a plurality of calibration measurement sequences in which the test sensor units of the plurality of test sensor units are exposed 256 to a sequence of varying environmental conditions, wherein the environmental conditions are characterized at least by one or more environmental parameters including a concentration of the target gas.

According to an example, wherein the determining 1002 of the calibrated measurement value 132 comprises using a baseline value 244, e.g. of the sensing unit 110 of the gas sensing device 100.

According to an example, the method 1000 further comprises steps of:
  determining an operational condition of the gas sensing device 100, and
  switching the calibration model 120 in response to a change of the operational condition.

According to an example, the method 1000 further comprises obtaining a further measurement signal 112' from a further measurement unit 110', and wherein the method 1000 comprises determining the calibrated measurement value 132 based on the measurement signal 112 and the further measurement signal 112', and wherein the method 1000 further comprises:
  evaluating 472, 473, 474 the further measurement signal 112' so as to decide whether the further sensing unit 110' is in a malfunctioning state,
  if the evaluation of the further measurement signal indicates, that the further sensing unit 110' is in a malfunctioning state,
  determining the calibrated measurement value 132 independent of the further measurement signal 112', and/or
  using 476, as the calibration model 120, a further calibration model 120' which is independent of calibration data from test sensing units of the type of the further sensing unit.

According to an example, the method 1000 further comprises obtaining an information about a location of the gas sensing device 100, and using 478, as the calibration model

120, a calibration model which is based on calibration data which is representative of the location.

According to an example, the method 1000 further comprises characterizing an environment of the gas sensing device 100 by evaluating an evolution of the measurement signal during a period of time, and selecting, as the calibration model 120, a calibration model on the basis of the characterization of the environment of the gas sensing device 100.

According to an example, the method 1000 further comprises receiving a further calibration model, and using the further calibration model as the calibration model.

According to an example, the method 1000 further comprises selecting the calibration model for the determination of the calibrated measurement value 132 from a plurality of calibration models.

According to an example, the method 1000 further comprises detecting 893 whether an exposure of the gas sensing device 100 to the target gas exceeds a first threshold, determining 894 a baseline value, e.g. for a sensing unit of the gas sensing device, if the exposure of the sensor unit to the target gas exceeds the first threshold, and using the determined baseline value as an input for the calibration model 120 so as to determine the calibrated measurement value 132.

According to an example, the method 1000 further comprises detecting 995 whether an exposure 992 of the gas sensing device 100 to the target gas exceeds a second threshold, and initializing a recovery sequence 999, if the exposure of the gas sensing device 100 to the target gas exceeds the second threshold.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

Some or all of the method steps may be executed by (or using) a hardware apparatus, like for example, a microprocessor, a programmable computer or an electronic circuit. In some embodiments, one or more of the most important method steps may be executed by such an apparatus.

Depending on certain implementation requirements, embodiments of the invention can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory.

A further embodiment of the inventive method is, therefore, a data stream or a sequence of signals representing the computer program for performing one of the methods described herein. The data stream or the sequence of signals may for example be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer.

The methods described herein may be performed using a hardware apparatus, or using a computer, or using a combination of a hardware apparatus and a computer.

In the foregoing Detailed Description, it can be seen that various features are grouped together in examples for the purpose of streamlining the disclosure. This method of disclosure is not to be interpreted as reflecting an intention that the claimed examples require more features than are expressly recited in each claim. Rather, as the following claims reflect, subject matter may lie in less than all features of a single disclosed example. Thus the following claims are hereby incorporated into the Detailed Description, where each claim may stand on its own as a separate example. While each claim may stand on its own as a separate example, it is to be noted that, although a dependent claim may refer in the claims to a specific combination with one or more other claims, other examples may also include a combination of the dependent claim with the subject matter of each other dependent claim or a combination of each feature with other dependent or independent claims. Such combinations are proposed herein unless it is stated that a specific combination is not intended. Furthermore, it is intended to include also features of a claim to any other independent claim even if this claim is not directly made dependent to the independent claim.

The above described embodiments are merely illustrative for the principles of the present disclosure. It is understood that modifications and variations of the arrangements and the details described herein will be apparent to others skilled in the art. It is the intent, therefore, to be limited only by the scope of the pending patent claims and not by the specific details presented by way of description and explanation of the embodiments herein.

What is claimed is:

1. A gas sensing device for sensing a target gas, the gas sensing device comprising:
   a sensing unit for sensing the target gas, the sensing unit being configured for providing a measurement signal based on a concentration of the target gas in an environment of the gas sensing device;
   a signal calibration unit, configured for determining a calibrated measurement value based on the measurement signal and based on a calibration model,
   wherein the calibration model is based on calibration data of a plurality of test sensor units having a same type as the sensing unit, and
   wherein the signal calibration unit is further configured for, in response to determining malfunctioning of the gas sensing device, switching the calibration model to a second calibration model for the sensing unit.

2. The gas sensing device according to claim 1, wherein the calibration data includes measurement signal values of the test sensor units acquired during a plurality of calibration measurement sequences in which test sensor units of the plurality of test sensor units are exposed to a sequence of varying environmental conditions, wherein the environmental conditions are characterized at least by one or more environmental parameters including a concentration of the target gas.

3. The gas sensing device according to claim 1, wherein the calibration model is a statistical model which is trained by supervised learning techniques using the calibration data.

4. The gas sensing device according to claim 1, wherein the calibration data of the test sensor units includes respective baseline values of the test sensor units.

5. The gas sensing device according to claim 1, wherein the gas sensing device comprises a further sensing unit for sensing a further target gas, and
   wherein the test sensor units of the plurality of test sensor units have the same types as the sensing unit and the further sensing unit, and wherein the calibration data includes measurement signal values of the test sensor units acquired during a plurality of calibration measurement sequences in which the test sensor units of the plurality of test sensor units are exposed to a sequence of varying concentrations of at least one of the target gas and the further target gas.

6. The gas sensing device according to claim 1, wherein the gas sensing device further comprises a data storage holding a baseline value, and wherein the signal calibration unit is configured for using the baseline value for determining the calibrated measurement value.

7. The gas sensing device according to claim 1, wherein the gas sensing device further comprises:
   means for determining an operational condition of the gas sensing device.

8. The gas sensing device according to claim 1, wherein the gas sensing device comprises a further sensing unit for sensing a further target gas, the further sensing unit being configured for providing a further measurement signal based on a concentration of the further target gas in the environment of the gas sensing device, wherein the signal calibration unit is configured for determining the calibrated measurement value based on the measurement signal and the further measurement signal, and wherein the gas sensing device further comprises:
   means for evaluating the further measurement signal so as to decide whether the further sensing unit is in a malfunctioning state, and
   wherein the signal calibration unit is configured for, if the evaluation of the further measurement signal indicates, that the further sensing unit is in a malfunctioning state,
   determining the calibrated measurement value independent of the further measurement signal, and/or
   using, as the calibration model, a further calibration model which is independent of calibration data from test sensing units of the type of the further sensing unit.

9. The gas sensing device according to claim 1, further comprising means for obtaining an information about a location of the gas sensing device,
   wherein the signal calibration unit is configured to use, as the calibration model, a calibration model which is based on calibration data which is representative of the location.

10. The gas sensing device according to claim 1, further comprising means for characterizing an environment of the gas sensing device by evaluating an evolution of the measurement signal during a period of time,
    wherein the signal calibration unit is configured to select, as the calibration model, a calibration model on the basis of the characterization of the environment of the gas sensing device.

11. The gas sensing device according to claim 1, further comprising means for receiving a further calibration model, and wherein the signal calibration unit is configured to use the further calibration model as the calibration model.

12. The gas sensing device according to claim 1, further comprising a data storage holding a plurality of calibration models, wherein the signal calibration unit is configured to select the calibration model for the determination of the calibrated measurement value from the plurality of calibration models.

13. The gas sensing device according to claim 1, wherein the gas sensing device further comprises
    means for detecting whether an exposure of the sensing unit to the target gas exceeds a first threshold; and
    means for determining a baseline value of the sensing unit if the exposure of the sensing unit to the target gas exceeds the first threshold, and
    wherein the signal calibration unit is configured to use the determined baseline value as an input for the calibration model so as to determine the calibrated measurement value.

14. The gas sensing device according to claim 1, wherein the gas sensing device further comprises means for detecting whether an exposure of the gas sensing device to the target gas exceeds a second threshold, and
    wherein the gas sensing device comprises means for initializing a recovery sequence, if the exposure of the gas sensing device to the target gas exceeds the second threshold.

15. The gas sensing device according to claim 1, comprising a chemoresistive gas sensing device.

16. A method for determining a calibrated measurement value for a concentration of a target gas, the method comprising:

obtaining a measurement signal based on the concentration of the target gas from a sensor unit;

determining the calibrated measurement value based on the measurement signal and based on a calibration model, wherein the calibration model is based on calibration data of a plurality of test sensor units having a same type as the sensor unit;

determining malfunctioning of the gas sensing device; and in response to determining the malfunctioning, switching the calibration model to a second calibration model for the sensing unit.

17. The method according to claim 16, wherein the calibration data includes measurement signal values of the test sensor units acquired during a plurality of calibration measurement sequences in which test sensor units of the plurality of test sensor units are exposed to a sequence of varying environmental conditions, wherein the environmental conditions are characterized at least by one or more environmental parameters including a concentration of the target gas.

18. The method according to claim 16, wherein the calibration model is a statistical model which is trained by supervised learning techniques using the calibration data.

19. The method according to claim 16, wherein the calibration data of the test sensor units includes respective baseline values of the test sensor units.

20. A gas sensing device for sensing a target gas, the gas sensing device comprising:

a sensing unit for sensing the target gas, the sensing unit being configured for providing a measurement signal based on a concentration of the target gas in an environment of the gas sensing device;

a signal calibration unit, configured for determining a calibrated measurement value based on the measurement signal and based on a calibration model, wherein the calibration model is based on calibration data of a plurality of test sensor units having a same type as the sensing unit, and wherein the signal calibration unit is further configured for:

in response to determining a malfunctioning of the gas sensing device, switching the calibration model to a second calibration model for the sensing unit;

detecting whether an exposure of the sensing unit to the target gas exceeds a first threshold;

if the exposure of the sensing unit to the target gas exceeds the first threshold, determining a first baseline value of the sensing unit; and using the first baseline value as an input for the calibration model to determine the calibrated measurement value.

* * * * *